US012735674B1

(12) United States Patent
Gonzalez

(10) Patent No.: US 12,735,674 B1
(45) **Date of Patent: *Sep. 15, 2026**

(54) CELLULOSE CONSTRUCTS BASED ON GAS VESICLES AND BACTERIAL CELLULOSE

(71) Applicant: Lina Gonzalez, Worcester, MA (US)

(72) Inventor: Lina Gonzalez, Worcester, MA (US)

( * ) Notice: Subject to any disclaimer, the term of this patent is extended or adjusted under 35 U.S.C. 154(b) by 285 days.

This patent is subject to a terminal disclaimer.

(21) Appl. No.: 18/129,376

(22) Filed: Mar. 31, 2023

(51) Int. Cl.
*C12N 1/22* (2006.01)
*C08L 1/02* (2006.01)
*C12N 1/20* (2026.01)

(52) U.S. Cl.
CPC .................. *C12N 1/22* (2013.01); *C08L 1/02* (2013.01); *C12N 1/20* (2013.01); *C12N 2500/34* (2013.01); *C12N 2500/76* (2013.01); *C12N 2510/02* (2013.01); *C12N 2533/78* (2013.01)

(58) Field of Classification Search
None
See application file for complete search history.

(56) References Cited

U.S. PATENT DOCUMENTS

| | | | | |
|---|---|---|---|---|
| 12,280,348 | B2 * | 4/2025 | Gonzalez | C08L 1/02 |
| 2014/0288411 | A1 * | 9/2014 | Shapiro | A61K 49/1809 530/391.1 |
| 2014/0364381 | A1 * | 12/2014 | Ju | A61L 15/48 604/304 |
| 2018/0030501 | A1 * | 2/2018 | Bourdeau | C12N 15/74 |

OTHER PUBLICATIONS

Volkner et al., "Accessory Gvp Proteins Form a Complex During Gas Vesicle Formation of Haloarchaea" Frontiers in Microbiology vol. 11 pp. 1-13, DOI:10.3389/fmicb.2020.610179 (Year: 2020).*

Portela et al., "Bacterial Cellulose: a versatile biopolymer for wound dressing applications" microbial biotechnology vol. 12 No. 4 pp. 586-610, doi:10.1111/1751-7915.13392 (Year: 2019).*

Stergar et al., "Review of aerogel-based materials in biomedical applications" J Sol-Gel Sci Technol vol. 77 pp. 738-752, DOI: 10.1007/s10971-016-3968-5 (Year: 2016).*

Oliveira et al., "Synthesis and characterization of microcrystalline cellulose produced from bacterial cellulose" J Therm Anal Calorim vol. 106 pp. 703-709, DOI: 10.1007/s10973-011-1449-1 (Year: 2011).*

Trache et al., "Microcrystalline cellulose: Isolation, characterization and bio-composites application—A review" International Journal of Biological Macromolecules vol. 93 pp. 789-804, DOI: 10.1016/j.ijbiomac.2016.09.056 (Year: 2016).*

Valo et al., "Immobilization of protein-coated drug nanoparticles in nanofibrillar cellulose matrices—Enhanced stability and release" Journal of Controlled Release vol. 156 pp. 390-397, doi:10.1016/j.jconrel.2011.07.016 (Year: 2011).*

Janecek et al., "Structural and evolutionary aspects of two families of non-catalytic domains present in starch and glycogen binding proteins from microbes, plants, and animals" Enzyme and Microbial Technology vol. 49 pp. 429-440, DOI: 10.1016/j.enzmictec.2011.07.002 (Year: 2011).*

(Continued)

*Primary Examiner* — Andrea Olson
(74) *Attorney, Agent, or Firm* — Brian M. Dingman; Prince Lobel Tye, LLP

(57) ABSTRACT

A material with a scaffold comprising a series of at least partially spaced fibers and gas vesicles locates between fibers. The gas vesicles comprise external anchoring modules that are effective to anchor the gas vesicles to the fibers.

15 Claims, 22 Drawing Sheets

(56) References Cited

OTHER PUBLICATIONS

Honda et al., "Stoichiometrically controlled Immobilization of Multiple Enzymes on Magnetic Nanoparticles by the Magnetosome Display System for Efficient Cellulose Hydrolysis" Biomacromolecules vol. 16, pp. 3863-3868DOI:10.1021/acs.biomac.5b01174 (Year: 2015).*

* cited by examiner

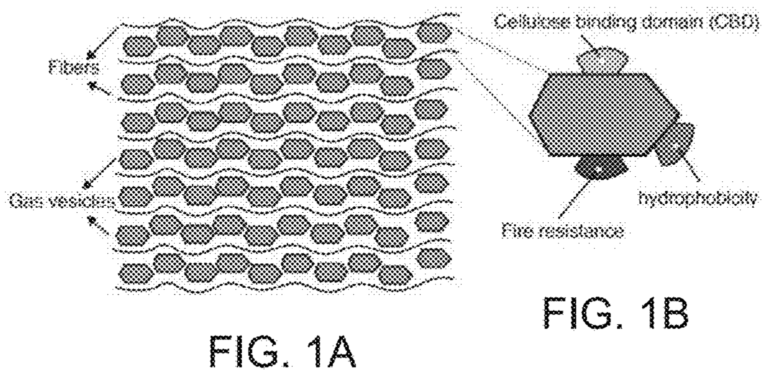
FIG. 1A
FIG. 1B
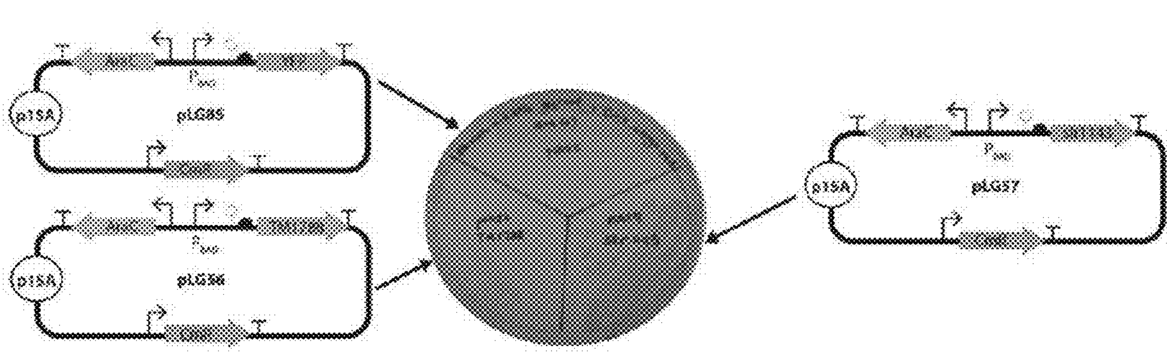
FIG. 2

% of concentrated GVs in mixtures

Size of plasmid
AmpR marker
Origin of replication (p15A)
homology back
SpR marker
Lac I
homology front
(6.3 kb)
RBS Pspank
(10.4 kb)

(12 kb)
Remove
Add (11 kb)

(12.2 kb)

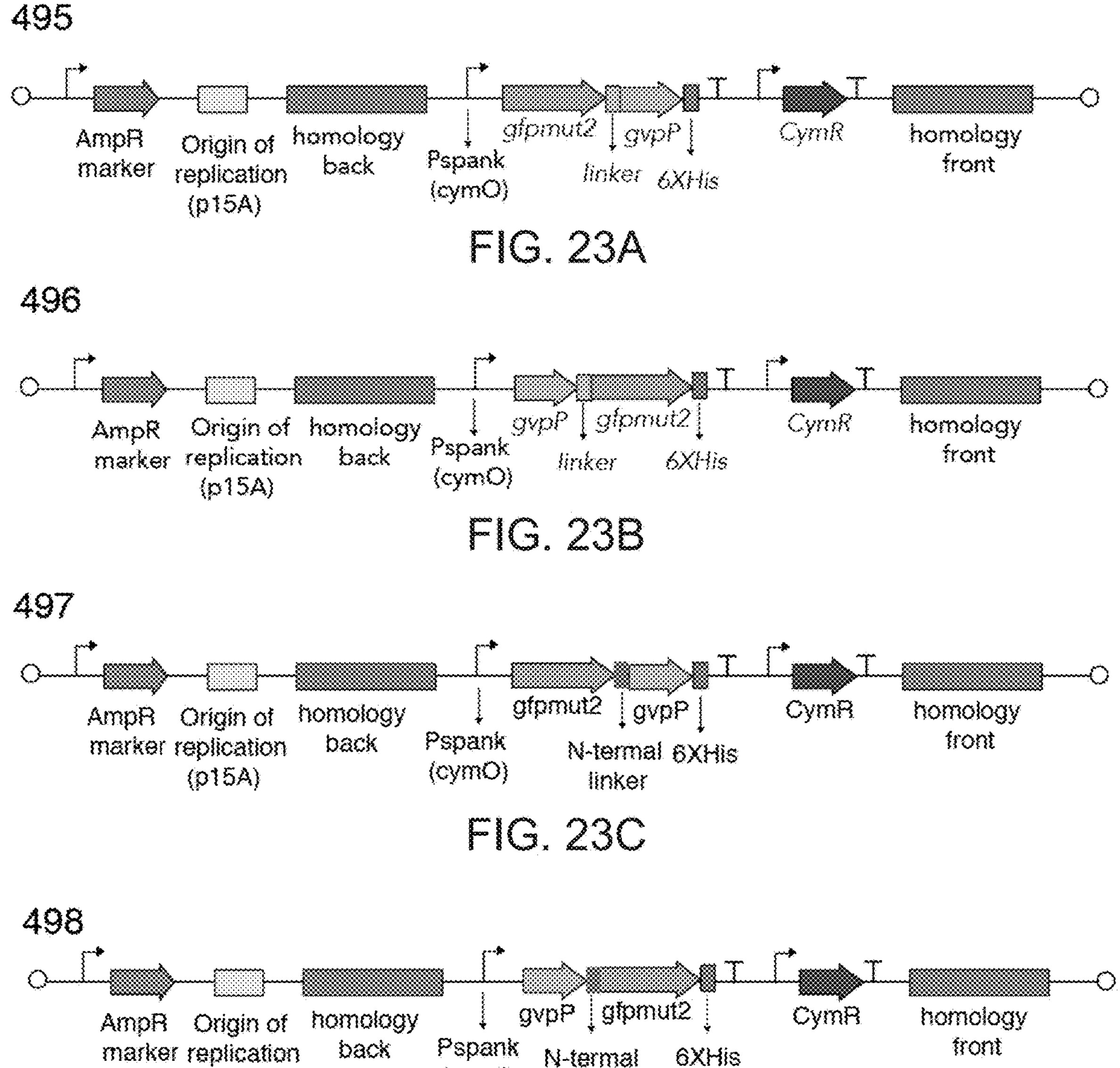
495
AmpR marker
Origin of replication (p15A)
homology back
Pspank (cymO)
gfpmut2
linker
gvpP
6XHis
CymR
homology front
FIG. 23A
496
AmpR marker
Origin of replication (p15A)
homology back
Pspank (cymO)
gvpP
linker
gfpmut2
6XHis
CymR
homology front
FIG. 23B
497
AmpR marker
Origin of replication (p15A)
homology back
Pspank (cymO)
gfpmut2
N-termal linker
gvpP
6XHis
CymR
homology front
FIG. 23C
498
AmpR marker
Origin of replication (p15A)
homology back
Pspank (cymO)
gvpP
N-termal linker
gfpmut2
6XHis
CymR
homology front
FIG. 23D

CELLULOSE CONSTRUCTS BASED ON GAS VESICLES AND BACTERIAL CELLULOSE

GOVERNMENT RIGHTS

This invention was made with government support under Award ID 2050101 awarded by the National Science Foundation (NSF). The government has certain rights in the invention.

CROSS-REFERENCE TO RELATED APPLICATIONS

This application is a continuation in part of application Ser. No. 17/391,352, filed in the U.S. Patent Office on Aug. 2, 2021, which itself claims priority of Provisional Patent Application Ser. No. 63/059,303 filed on Jul. 31, 2020. This application also claims priority of Provisional Patent Application 63/362,245 filed on Mar. 31, 2022. The disclosures of each of these prior applications are incorporated herein by reference in their entireties.

BACKGROUND

This disclosure relates to a cellulose construct such as an aerogel.

Bacterial cellulose (BC) has played an important role in the bioeconomy, specifically in the medical and the food industries. Its roles stem from its high-water retention capacity, biocompatibility, resistance to biodegradation and high purity. Specifically, there are a wealth of applications in the medical field such as skin care, skin tissue repair, artificial dura matter, blood vessels and connective tissues. For example, this BC material helps accelerate the rate of healing mimicking the body's extracellular matrix (ECM) and the never-dried wound provides cooling and therefore burn pain relief. Other non-biomedical applications include using the cellulose network as a carrier for catalytic reactions for adsorption of oil spills in aquatic environments, and for making moisturizing facial masks (BOWIL Biotech). In food applications, it has been used as a low-calorie and high-fiber food additive to emulsify, stabilize and modify texture. BC has been used to make nata de coco, sweetened jelly-like cubes that originated in the Philippines. Due to its high thermal resistance (up to 300° C.) it can withstand the processing temperatures of electronics devices and, thus it can be used as a dielectric spacer in semiconductors. BC's strength and light weight allowed Sony to use it as a speaker diaphragm in headphones.

*Gluconoacetobacter xylinus* is known as the most prolific cellulose producer. In a concerted manner and via a sophisticated glycosyltransferase (GT) molecular machinery, this organism spins out single glucan chains while UDP-glucose are fed, assembled and translocated through tiny pores normal to the cell membrane. There is a hierarchical architecture in the formation of cellulose mat with single glucan chains or elementary fibrils (1.5-3.5 nm) forming microfibrils (10-30 nm) which are subsequently organized into stiff bundled fibers on the order of 100 nm as the bacteria concomitantly undergoes cells division. It is speculated that these cells may be polymerizing ~200,000 glucose units per sec., per cell.

Cellulose extracted from trees contains other compounds such as lignin and hemicellulose that act as the glue that holds the cellulose fibers together. Artificial interpenetrating cellulose networks have been made specifically to reinforce the cellulose network with carbon nanotubes. To name a few, calcium deficient hydroxyapatite, acrylic acid (AAc), soy protein isolate and nanosilver have been incorporated into the cellulose network with resultant applications in bone colonization, heavy metal waste purification, and to prevent wound infections, respectively.

SUMMARY

Disclosed herein is the use of bacterial cellulose as the structural support for making an insulation material.

Bacterial cellulose (BC) serves as a scaffold material for an aerogel, and provides the structural integrity needed for the product to prevent slumping or to maintain it in an upright position. At the same time, this material is compliant and moldable so as to fit into a stud cavity. BC has a young's modulus ~138 GPa and tensile strength of 2 GPa (on par with Kevlar fibers). Gas vesicles can be incorporated into the cellulose network, forming a new composite material with a functional architecture.

The cellulose network is already porous (254±76.65 nm), but having the gas vesicles embedded in them further constrict the size of the pores throughout the material, making it an effective insulator. Essentially, this method permits the anchoring of the fibers and helps close the larger gaps in the cellulose network with the gas vesicle acting as the molding "receptacles." Using genetic engineering tools will provide a flexible platform for modifying the scaffold and gas vesicles with the necessary chemistries.

Gas vesicles allow positioning of the *Halobacterium salinarum* cells within an optimal water column for nutrients and gasses. Cells exposed to oxygen limiting conditions upregulate the gas vesicle synthesis. In the photosynthetic bacteria, *Anabaena flos-aquae*, carbohydrate synthesis serves as ballast, while gas vesicles act as buoyant devices to raise these organisms to the surface where light is available. Gasses diffuse freely into the gas vesicles, but they are impermeable to water due to the high surface tension of the hydrophobic interior. The gas vesicles are cylindrical with conical caps or ends with an aspect ratio of approximately 2:1 (length to diameter) and lengths ranging from 0.1 to 2 μm. Thus, creating a process to selectively use vesicles on the order of the mean free path of air molecules (about 68 nm) could provide an R-value near that of an aerogel (R-value~10° F. ft$^2$ h/BTU). Gas vesicles have been used in biotechnology as image contrast agents in MRI.

Two of the well-studied genes responsible for the structural compositions of the gas vesicles are gvpA and gvpC. The GvpA protein acts as ribs for the cylindrical cage and the GvpC protein strengthen the gas vesicles by providing an exterior mesh. This mesh increases the pressure needed to collapse the compartment. The GvpA protein of these vesicles acts as the "ribs" with α-helices and β-turns and the wall thickness of these vesicles is 2 nm. Using synthetic biology tools, the structural genes, gvpC and gvpA, can be modified to display a cellulose binding domain to secure the vesicles to the fibers.

Essentially, what has been fabricated with these biological organisms are porous structures or a special kind of aerogel. Aerogel was invented in the year 1931, but due to the cost of production its wide used and availability has been hampered. Aerogels are composed of mostly air (>90% porosity) and possess a thermal conductivity lower than that of air as the gasses have a tough time diffusing through the nanoporous cavities (<70 nm). Aerogels are extremely light with density between 0.001 and 0.2 g/cm$^3$ and have high specific surface area between 200 and 600 m$^2$/g. Aerogels have been used by NASA during the Mars Exploration to keep the rover vehicle from losing heat and in the Stardust spacecraft as a collector to trap high speed interstellar particles. In the oil industry, aerogel plays a crucial role as a lightweight insulator for oil pipes with a pipe-in-pipe configuration for underwater mining. As a result of having excellent thermal insulation properties, a thin piece of aerogel is sufficient to assure the fluidity of the oil in the freezing cold water. At the same time, it reduces the weight of the pipelines, thus preventing a boat from capsizing. Aerogels are especially desirable where a thin piece of insulation is needed or where space is limited. Due to the large surface-specific area, aerogels are widely used in adsorption applications.

To make an aerogel and prevent collapsing and shrinkage due to capillary forces either supercritical drying or freeze-drying methods are used. In supercritical drying, solvent exchange is implemented. With such, water is replaced by a solvent (e.g. ethanol) and the material is then subjected to purging with $CO_2$. When a critical high pressure is reached, $CO_2$ is completely dissolved in the solvent, which lowers the liquid gas interfacial forces to zero. At this point, the solvent can be removed without dragging the walls and retaining the 3D structural network.

Instead of replacing the liquid with gasses as is done with $CO_2$ in supercritical drying and with sublimation as in freeze-drying, in our method, the gasses are already present in the material. Integrating gas vesicles in the media is a completely new method to create open porous networks. Cellulose has a high water retention capacity; thus in a sense, through genetic engineering (through changing the surface chemistry), the capacity of the network to retain water is altered so as to retain air (gas vesicles) instead. The envelop of the gas vesicles serves as an interphase for conducting the necessary chemistries. In essence, the material will not have to dry due to its hydrophobic properties and its presence at the boundary due to its acquired buoyancy.

All examples and features mentioned below can be combined in any technically possible way.

In one aspect, a material includes a scaffold comprising a series of at least partially spaced fibers, and gas vesicles locates between fibers. The gas vesicles comprise external anchoring modules that are effective to anchor the gas vesicles to the fibers.

Some examples include one of the above and/or below features, or any combination thereof. In an example the material is an aerogel. In an example the scaffold comprises bacterial cellulose. In an example the bacterial cellulose is produced by a genetically modified bacterium. In an example the external anchoring modules of the gas vesicles comprise cellulose binding modules. In an example the cellulose binding modules comprise CBM48 from *Komagataeibacter sucrofermentans* and *Micromonas pusilla*. In an example the gas vesicles further comprise external hydrophobicity modules. In an example the gas vesicles further comprise external fire resistance modules.

In another aspect a method of creating gas vesicles includes using a genetically-modified bacterium to produce gas vesicles that comprise external anchoring modules that are effective to anchor the gas vesicles to fibers.

Some examples include one of the above and/or below features, or any combination thereof. In an example the gas vesicles further comprise external hydrophobicity modules. In an example the gas vesicles further comprise external fire resistance modules.

In another aspect, a biodegradable plastic material includes at least one layer of cellulose derived from a bacterial strain, wherein at least one layer is treated with a plasticizer and dried.

Some examples include one of the above and/or below features, or any combination thereof. In an example the plasticizer comprises glycerol. In an example the plasticizer has a glycerol content of up to 1%. Further included is a material made from stacked layers of this plastic material.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the inventions. In the figures, identical or nearly identical components illustrated in various figures may be represented by a like reference character or numeral. For purposes of clarity, not every component may be labeled in every figure. In the figures:

FIGS. 1A-1B. Gas vesicles and cellulose hybrid material. FIG. 1A: Assembled fibers and gas vesicles FIG. 1B: genetically engineering a gas vesicle platform to have CBD, hydrophobicity and fire-retardant properties.

FIG. 2. Overexpression of diguanylate cyclase. The shown plasmids are expressed in *E. coli* BL21 with control plasmids expressing YFP. Plasmid expressing a TM1788 gene from *T. maritima* and an slr1143 gene from *Synechocystis* sp. (strain PCC 6803).

FIG. 3A: circuit diagram of RSF1010 origin vector with the sfgfp gene FIG. 3B: Anderson's promoters (J23XXX) tested in this vector and expressed in *G. xylinus * FIG. 3C: Electroporation transformation efficiency in *G. xylinus*.

* FIG. 4A: circuit diagram with the slr1143 gene driven with the Anderson promoters FIG. 4B: Growth curve of engineered *G. xylinus* strains Gx 60, Gx61 and Gx216 and comparison against the wild type strains FIG. 4C: Cellulose production quantification before and after drying the samples.

FIG. 9A: gyp gene cluster FIG. 9B: Cuminic acid circuit to tune expression of chimeric protein. FIG. 9C: Production, lysis and self-assembly of genetically modified gas vesicles within the cellulose fibers.

FIG. 10A: Construct to modify the fibers with BslA FIG. 10B: Construct to modify the vesicles FIG. 10C: Assembly after secretion of protein complex into the media.

sugar content FIG. 11C: tea type and types of FIG. 11D: black teas. FIG. 11E: Titration of the apple cider vinegar without adjusting the pH FIG. 11F: using 50 mL of apple cider vinegar and adjusting the pH of the media. FIG. 11G: Days grown on plates before measuring the thickness of the mat. FIG. 11H: Time of growth in shake flask before transferring to plates for the WT and the fast-growing Gx 60 strain.

FIGS. 12A-12C. Examining the oxygen conditions for best growth. FIG. 12A: Growth results with and without pumps. FIG. 12B: Results from purging the media with $N_2$ and adding 1 g of charcoal into the media. The control has no treatment. FIG. 12C: Tracking the dissolved oxygen content in the media. A mat is observed after oxygen is depleted from the media. For WT is about 2.5 days.

FIG. 13A: Schematic of growth procedure FIG. 13B: Testing weather sample cells at a specific optical density (OD) helps with growth. FIGS. 13C and 13D: After back diluting the cells to $OD_{600}$=0.1, the cells are grown for X days as shown in the x-axis. FIG. 13C: cells grown in small dishes (5" by 7") and FIG. 13D: cells grown in the larger trays (1'×1.5').

FIG. 14A: Comparing 1 L vs 2 L of media to grow cells in the 1.5 sq. ft. trays FIG. 14B: Determining optimal media volumes in dishes (5"×7") FIG. 14C: Increasing the concentration of sugars by 2X and FIG. 14D: 3X. In FIGS. 14C and D we did the experiments with the small 5" by 7" dishes.

FIG. 15A: Micrograph of an *H. salinarum* after purification FIG. 15B: TEM of extracted purified gas vesicles (GV).

FIG. 16A: Difference in thermal conductivity between control (no GVs) and experimental samples with GVs mixed with agar FIG. 16B: GVs mixed up with low melting temperature agarose after drying for 5 and 6 days FIG. 16C: same data as in FIG. 16B showing the % difference between control and the experimental group.

FIG. 17A: SEM picture of control (no GVs added) FIG. 17B: 25% of GVs added FIG. 17C: 50% of GVs added and FIG. 17D 75% of GVs added.

FIG. 18A: Plasmid 450 #11 with a p15A origin FIG. 18B: Plasmid 451 #6 with some parts of the gyp gene cluster FIG. 18C: Plasmid 457 #8 with all of the parts of the gene cluster and driven by the natural promoter FIG. 18D: Plasmid 492 #28 and #31 harbored on a host broad vector with the RSF1010 backbone FIG. 18E: Plasmid 506 #5 is the same as in FIG. 18D but with a weak constitute promoter.

FIG. 19A: These micrographs show the cells (492 #28 and #31) grown at low and high oxygen conditions. FIG. 19B: This micrograph (cell 506 #5) uses the circuit with a constitutive promoter and the same natural RBSs (FIG. 18 shows the corresponding genetic circuits for each cell).

FIG. 20A: Plasmid 450 #11 with a p15A origin FIG. 20B: Plasmid 454 #4 with some parts of the gyp gene cluster and without the homology back FIG. 20C: Plasmid 463 #1 with all of the parts of the gene cluster and driven by an IPTG inducible promoter FIG. 20D: Plasmid 467 #13 is a shorter version of 463 #1 missing genes A, P and Q and including the homology back FIG. 20E: Plasmid 505 #13 includes the whole gene cluster and the homology back and a Sp resistance marker.

FIG. 21A: These micrographs show the cells (467 #13) grown at 37° C. The white dots could be gas getting invaginated FIG. 21B: This micrograph show the gas vesicles growing them at 30° C.

FIGS. 23A-23D. Gene circuit to make fusion proteins of surface proteins GvpP on gas vesicles FIG. 23A-D: Circuits with different arrangement of the gene and using different linkers.

FIG. 24A; and FIG. 24C have plasmid #495 and #497, respectively. These images show the correlation between the refractile bodies (appear bright) and the florescence (bright image on dark background). FIG. 24B; and FIG. 24D: show cells with plasmid #496 and #498, respectively. Within these cells and the florescence loci are not present and GFP is diffused throughout the cells.

DETAILED DESCRIPTION

Figure 3A:
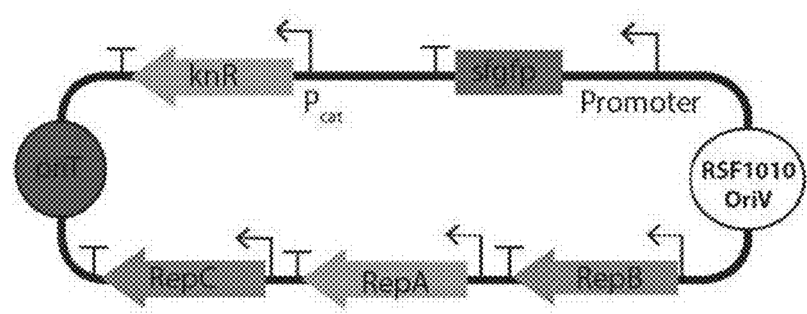
FIGS. 3A-3C. Genetic engineering tools to work with *G. xylinus*.

A method includes the development of a green insulation composite material that merges two biologically sourced materials: bacterial cellulose and gas vesicles (FIG. 1*a*). Fundamentally, the aerogel is made almost entirely out of biological organisms. An incentive to work on these materials is to step away from using non-renewable petroleum-based polymers and toxic products. Both of these biologically derived materials have a set of unique properties rendering them suitable for attaining the sought-after properties (insulating, strength to support itself and degree of pliability). Furthermore, both of these materials can be genetically modified to produce desired features to comply with regulations (FIG. 1*b*). A low thermal conductivity ($\lambda_{eff}$<25 mW/mK) and high R-value are critical parameters to develop a high-performance building insulation material. This will allow the material to develop an R-value close to or higher than R-6. Properties that should be achieved (in addition to thermal performance) are hydrophobicity (to prevent mold growth) and fire resistance. Normally, a separate vapor barrier is applied on the outer layer of an insulation material to keep it dry as insulation properties deteriorate when a material absorbs water.

Part 1: Establish chassis strains and work toward optimizing cellulose production.

Part 2: Add CBD to the gas vesicles to effectively anchor them to the cellulose fibers.

Part 3: Genetically engineer hydrophobicity and fire-retardant properties into the fibers.

Part 1: Establish Chassis Strains and Work Toward Optimizing Cellulose Production.

Culture set-up for growing the hybrid material and optimization of SCOBY culturing conditions.

There is an immense yield to field advantage in using bacterial cellulose. For example, a standard soccer field (70 m by 100 m) planted with trees would take 12-18 years before it could be harvested, and it would yield 3.5 tons of cellulose pulp after purification. Considering the same field size, culturing cellulose would take 10-15 days and yield 115 tons of cellulose. Moreover, arable land, fertilizer, pesticide, sunlight and the enormous amount of water used for growing trees are not needed. Moreover, the harsh downstream processing to remove lignin and hemicellulose are not required in the case of bacterial cellulose. Plant crops cannot be vertically stacked for growth whereas cellulose can as they do not require sunlight or direct contact with the soil.

Efforts have been made in replacing the commonly used expensive media, the Hestrin and Schramm (HS) media. At the moment the most economical and practical approach to grow bacterial cellulose is through using a symbiotic culture of bacteria and yeast (SCOBY). SCOBY is used to make a drink called Kombucha which is popular due to its antioxidant properties, probiotic benefits and propensity to reduce blood sugar level in Type 2 diabetes individuals. Using a SCOBY culture media eliminates the costly ingredient such as the yeast extract (the nitrogen source) used to prepare the HS media. The co-culture can be grown in readily available ingredients such as tea, sugar and apple cider. In the present disclosure the SCOBY recipe is used, adjusting the parameters such as tea type and pH. Only *G. xylinus* strains are grown, so as to increase the bacterial cellulose yield and avoid the growth of other sugar-consuming organisms within the culture.

It is hypothesized that upregulating the production of a dgc gene in *G. xylinus* would yield higher production. The enzyme, diguanylate cyclase, catalyzes the conversion of two guanosine triphosphate (GTP) into cyclic di-GMP[32] (c-di-GMP). The signaling molecule c-di-GMP, also present during biofilm formation, is known to activate the BscA-BscB protein complex by interacting with a PilZ domain, displacing a gating loop and opening the active site. As shown in FIG. 2, expressing the slr1143 (more prominent production) and the TM1788 genes upregulates production of amyloid fibrils in *E. coli* BL21 as demonstrated through a congo red assay.

Slow bacterial growth is a significant limiting factor when scaling up product for commercialization; therefore, engineering a strain that grows much faster will benefit the industry. By expressing the slr1143 gene with effective promoters (FIGS. 3*a* and 3*b*) that work well with *G. xylinus*, more cellulose is produced, and at the same time the growth rate is increased significantly, improved by 4 times (FIG. 4). Due to an improved electroporation method for transforming the cells, this transformation is possible (FIG. 3*c*).

Figure 3B:
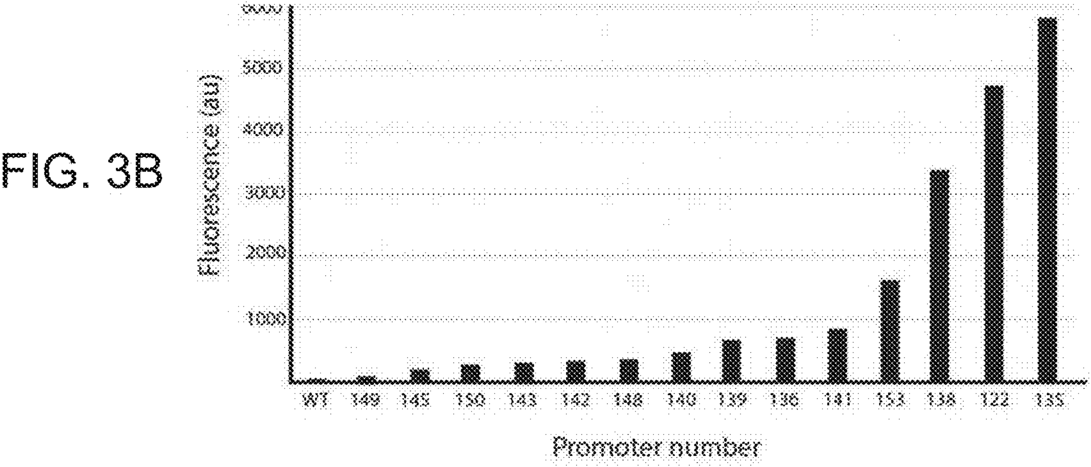
Figure 3C:
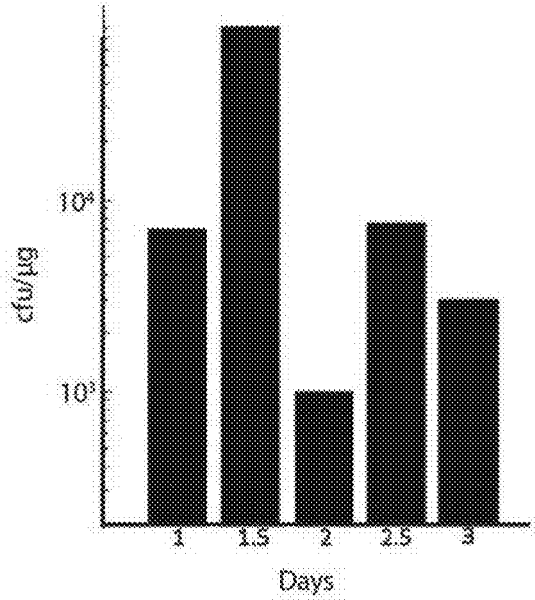
Figures 4A, 4B, 4C:
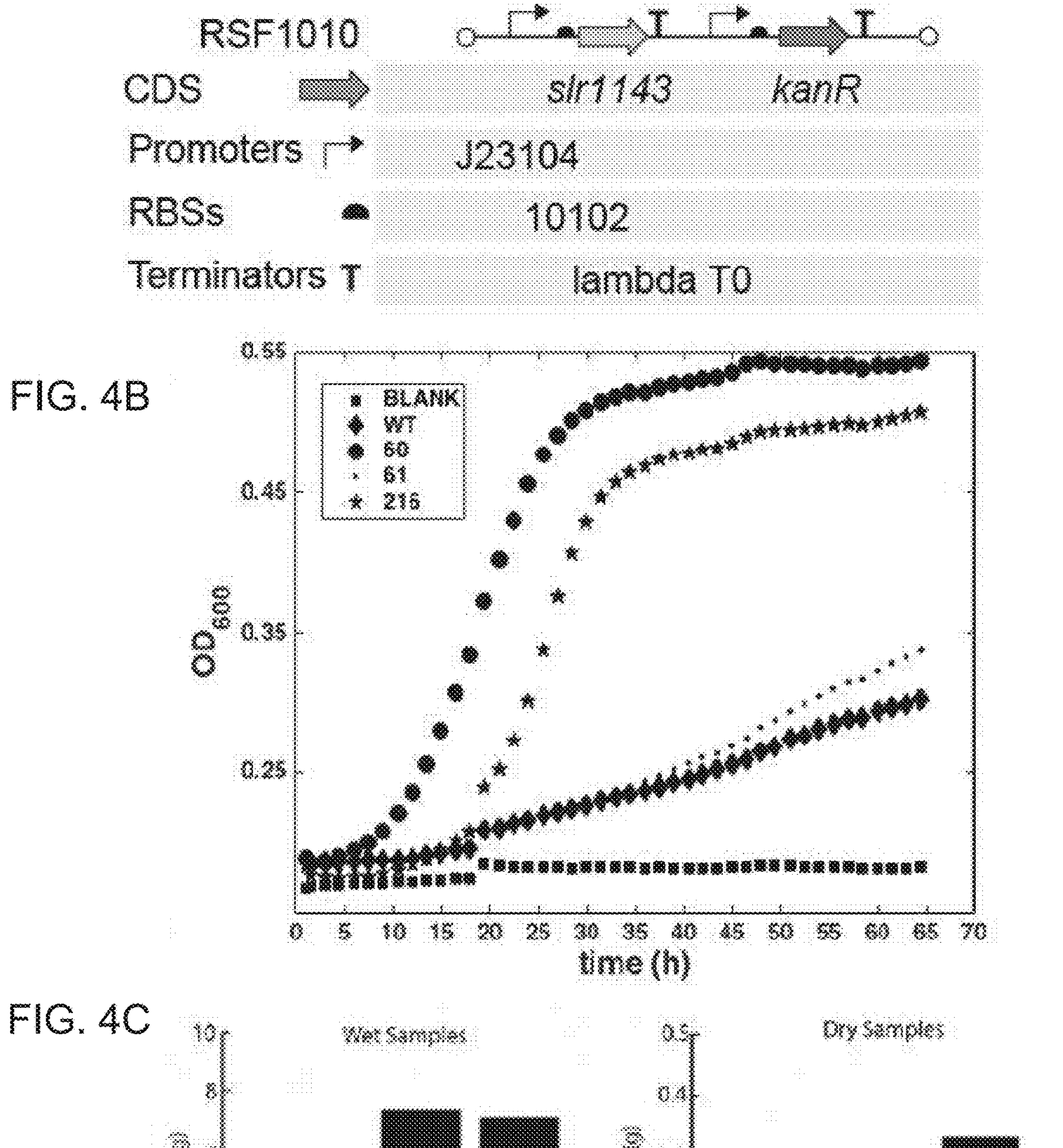
FIGS. 4A-4C. Improvement in growth rate curve and cellulose production of *G. xylinus

In addition, the Anderson promoters were tested, first in *E. coli*, then in *G. xylinus* cells shown in FIG. 3*b*, so as to tune the expression of these dgc genes. Multiple broad host vectors were tested and it was found that the one with a RSF1010 origin is able to replicate in agreement with the literature. Different antibiotics were tested and it was found that tetracycline, kanamycin, spectinomycin and ampicillin are good antibiotic candidates for selection whereas chloramphenicol and gentamycin are not. *G. xylinus* seems to have developed natural resistance to these antibiotics.

Processing of Cellulose Materials for Various Applications

Figure 5:
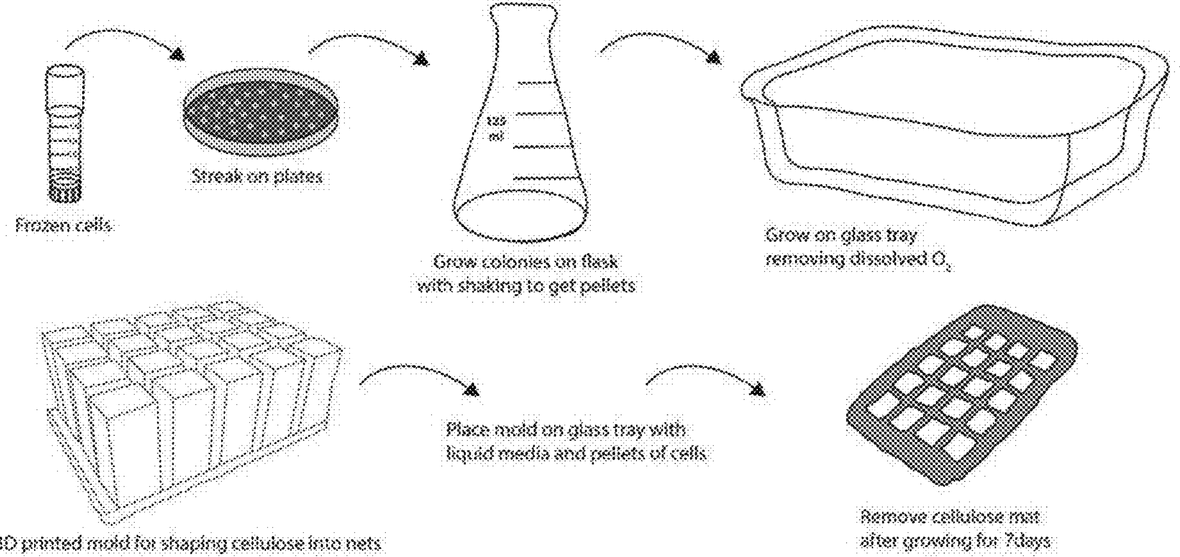
FIG. 5. Workflow for growing the *G. xylinus* cells and obtaining molded 3D printed nets.

After the cellulose material is dried, the material becomes fragile and breaks easily. Flexible cellulose sheets were produced by submerging and drying the material in a plasticizer glycerol (<5%). As shown in FIG. 5, the material is grown on glass trays, then the cells are removed with 2.5% NaOH, then rinsed with water and bleach. The material is subsequently washed and submerged in glycerol and let dry in metal racks. A glycerol content of 0.5 or 1% results in a smooth, clean (not sticky) texture. This will facilitate the usage of the material in a sewing machine. The resulting material can have dual functionality. It can be used as a biodegradable and compostable plastic material when a single or thin layer is utilized. It can be used as a green vegan leather material when the layers have been stacked together. The material becomes stronger with the addition of layers. The applications for these ranges from vegan leather bags and jackets, upholstery, footwear, clothing and automobile seats. Additionally, the cellulose material can be grown in a mold with a 3D printed grid (FIG. 5) to make nets for sporting goods, fishing nets, military cargos nets, safety nets, nets/mesh for packaging fruits, nature netting for trees (birds, mosquito) and medical nets.

3.5× Reduction in Media Cost and Optimization of Media

Figure 6:
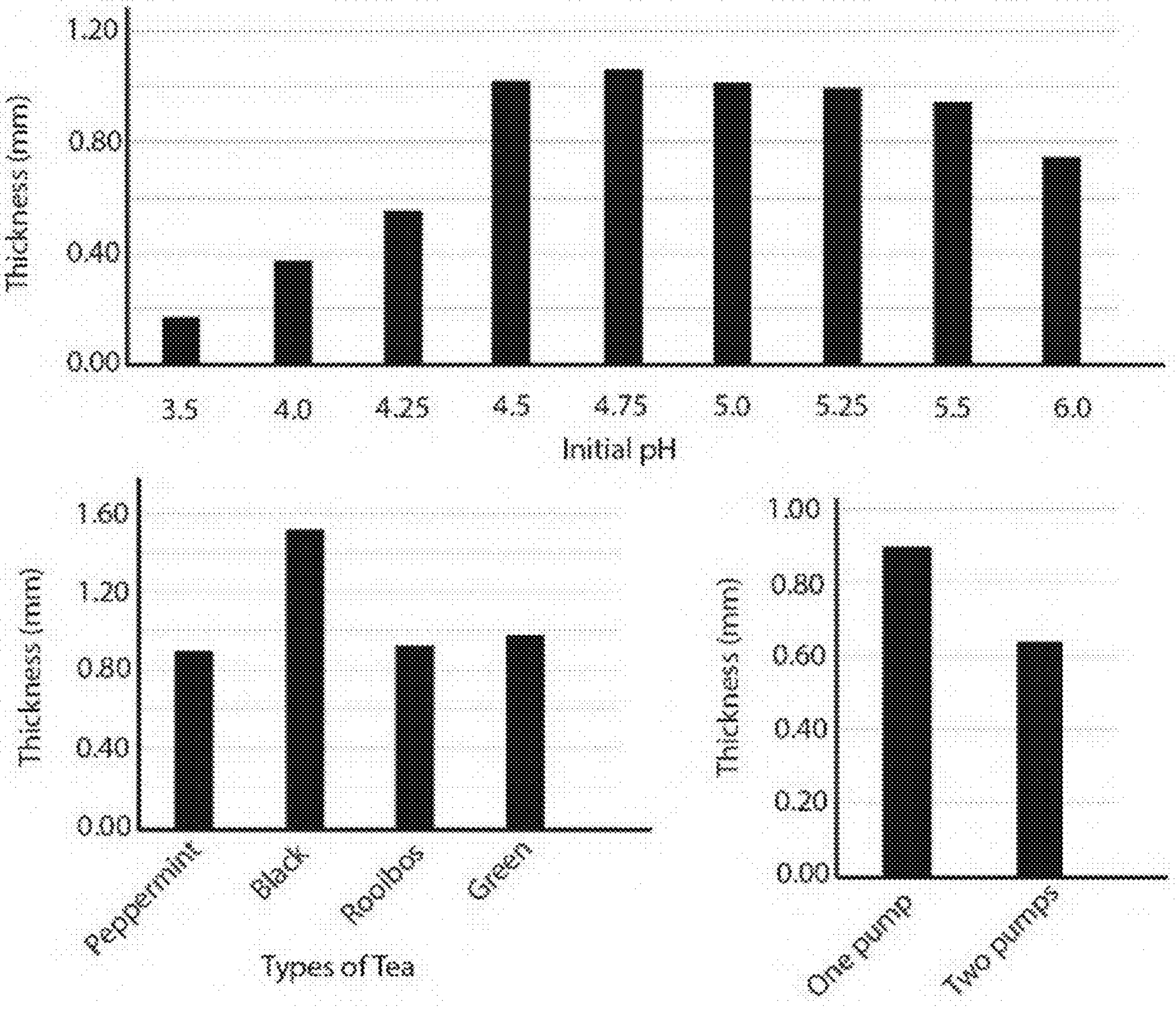
FIG. 6. Simple media optimization of pH, tea type and oxygen content.

A simple SCOBY media (presenting a 3.4× reduction in cost compared to the Hestrin Schram (HS) regularly used in academic labs) in the literature was modified significantly so that the cells produce thicker cellulose mat in less time (Table 1). It was found that an initial pH of 4.75 is ideal and black tea works best (FIG. 6). In addition, pumping air into the trays does not help with getting the cells to produce more cellulose. Cellulose production starts when the oxygen in the trays is completely depleted, but a high concentration of cells must be provided. The cells can be grown to a high density in shaking flasks then transferred to the trays.

TABLE 1

Cost comparison of the SCOBY media and the Hestrin and Schramm (HS)

| Ingredients | HS | K |
|---|---|---|
| Apple Cider Vinegar | | 0.38 |
| 1 Green tea bag | | 0.1 |
| Sugar | | 0.3 |
| SCOBY | | — |
| Glucose | 0.25 | |
| yeast extract | 1.07 | |
| peptone | 1.84 | |
| Na2HPO4 | 0.14 | |
| CITRIC acid | 0.21 | |
| Cost (1 L) | $3.51 | $0.78 |

Transferring the Gas Vesicle Machinery, the Gvp Gene Cluster to *B. subtilis* Making it Functional and Optimizing the Number of Vesicles in the Cells.

Figure 7:
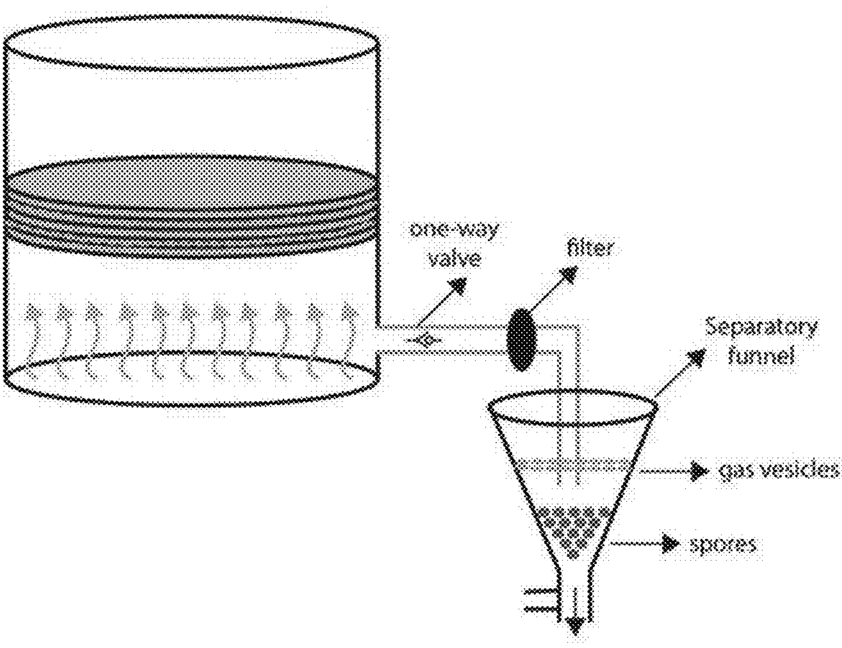
FIG. 7. Flow of the process for assembling the hybrid cellulose and gas vesicle materials.

*H. salinarum* doubles every 1.5 to 3 h and *B. subtilis* and *E. coli* double every 20 min when grown in Luria-Bertani broth (LB) at 37° C., under shaking conditions. This piece of information tells us that it impractical to use *H. salinarum* as our chassis for producing gas vesicles. This work requires the transferring of the gvp gene cluster to *B. subtilis* PY79 using readily available genetic tools. *B. subtilis* was chosen because is generally recognized as safe (GRAS status), grows fast, requires minimum nutrients, has an efficient secretion system and can sporulate. In regard to exploiting sporulation, the downstream processing for separating the gas vesicles from the cells can be facilitated by inducing sporulation. Ideally, gasses will rise to the surface and spores will sink to the bottom of a separatory funnel (see FIG. 7). After spores and cell debris at the bottom have been discard, the gasses left behind, floating at the surface of the funnel can be pumped to another container having the cellulose mat at the surface. Due to buoyancy of the gas vesicles, they once again will rise and lodge into the cellulose mat. In subsequent steps in the process, while the *G. xylinus* cells are weaving the cellulose fibers, the gas vesicle will be incorporated. Alternatively, the hybrid material can be created in a layer by layer fashion by alternating dipping the material between a gas vesicle bath and the growth media. Either of these methods will create a highly porous cellulose material.

Figure 8:
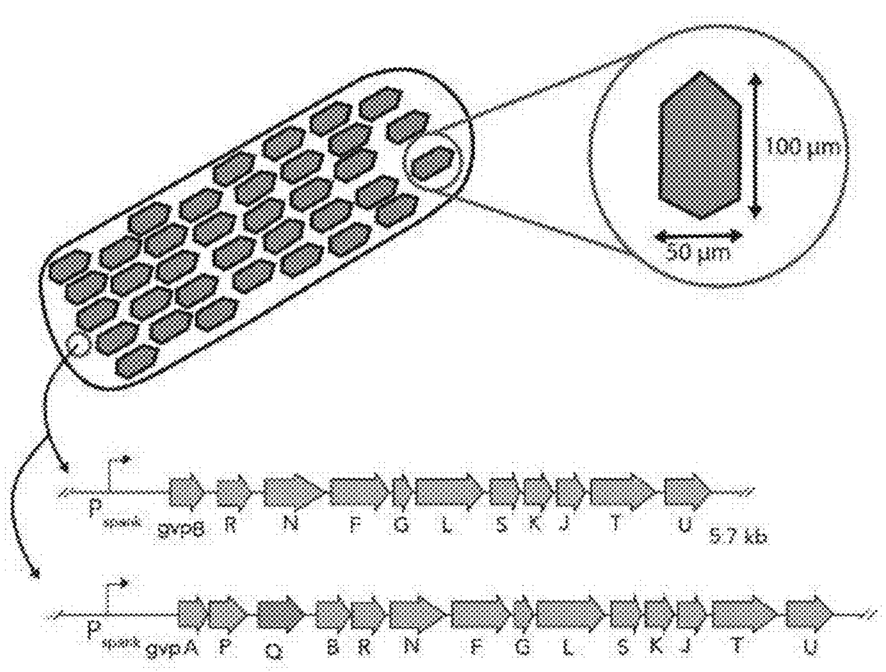
FIG. 8. Gyp cluster from *B. megaterium* and responsible for producing gas vesicles with the minimum sized (5.7 kb) and the entire cluster (7.0 kb).

The 7.0 kb gvp gene cluster (FIG. 8) found in *B. megaterium* will be integrated into the genome of *Bacillus subtilis* PY79 by homologous recombination via natural transformation (DNA uptake). In *B. megaterium*, this cluster is not functional as it might be induced under certain unknown conditions. New inducible promoters were developed that can be used to tune the expression level of this gene cluster. This cluster was previously moved to *E. coli*, but only the formation of bicones (first steps in gas vesicle formation) was achieved. The natural RBSs used in this work might not be properly translated in *E. coli*. Adequate expression of gas vesicles within the *B. subtilis* PY79 cells can be scrutinized via the buoyancy phenotype, TEM micrographs and phase contrast imaging (PCI) as these vesicles are refractile bodies (appearing as bright spots). The sequence with the gyp gene cluster for expression in *B. subtilis* is included in SEQ ID NO 3 (found in the parent application that is incorporated herein by reference). To find out more about this gene cluster, a BLAST search was conducted using the gvpQ gene and protein sequences, but no homology to other gvp genes was found. The software RADAR was used and it was determined that the gvpQ gene has 5 repeats so this might be the gvpC equivalent in other organisms. This can be tested by measuring the strength of the vesicles with and without this gene. This can be done using pressure nephelometry to determine the critical collapsing pressure of these gas vesicles. Scrutinizing and obtaining a basic understanding of this gene cluster will contribute to basic science and further understanding of these compartments can open new fields of inquiries and lead to new discoveries. Furthermore, screening for mutant cell producing gas vesicles with higher hydrostatic pressure would be useful.

To recover the gas vesicles the method used is cell lysis by inducing sporulation. The potential of gas vesicles disintegration (through protein degradation) due to specific proteases present in the cells for protein turnover is an issue. To circumvent this natural process, a protease deficient strain of *B. subtilis* K07 (available at BGSC) can be used. The parent strain for this strain is PY79 and it has seven proteases knockout. This will allow recovery of the gas vesicles passively (not requiring centrifugation), using an economical lysing method to release the vesicles.

Part 2: Add CBD to the Gas Vesicles to Effectively Anchor them to the Cellulose Fibers Modify the Structural Protein to Display the Cellulose Binding Domain (CBD)

Figure 9A:
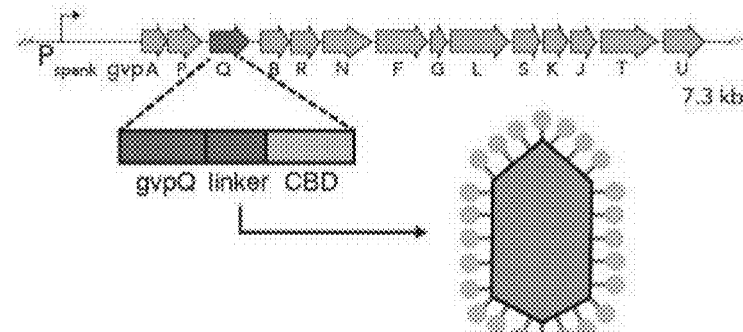
FIGS. 9A-9C. Adding a cellulose binding domain (CDB to the gas vesicles).
Figure 9B:
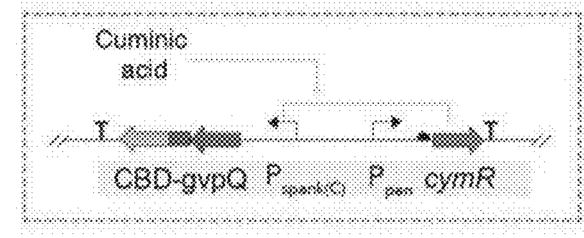
Figure 9C:
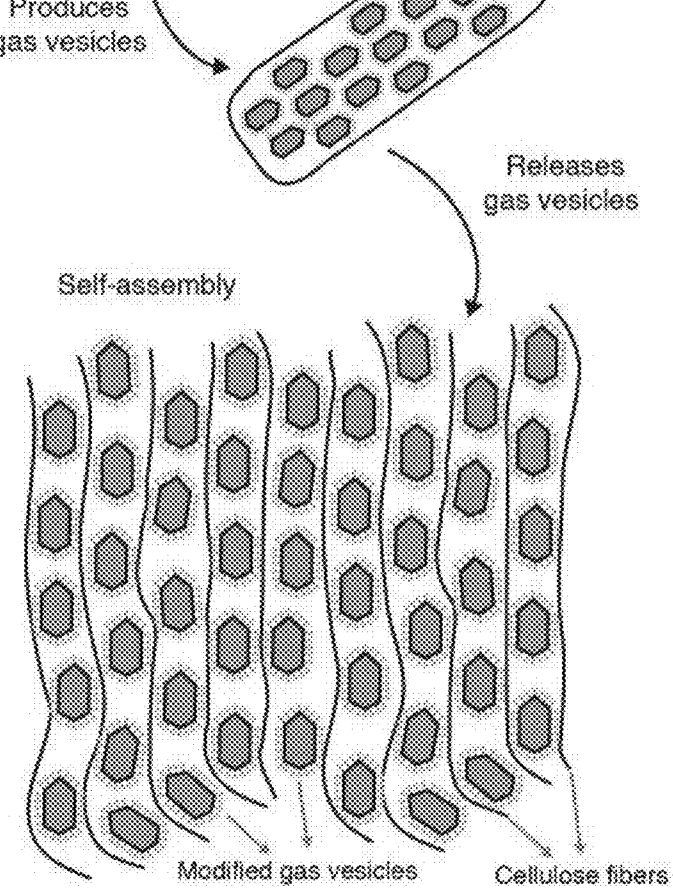
Figure 10A:
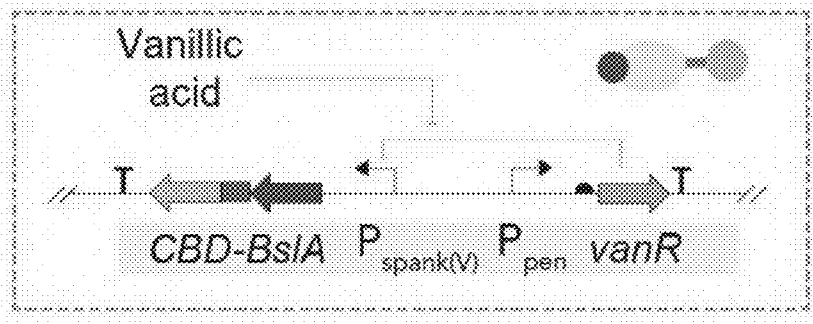
FIGS. 10A-10C. Transforming the cellulose mat into a hydrophobic material through genetically engineering.
Figure 10B:
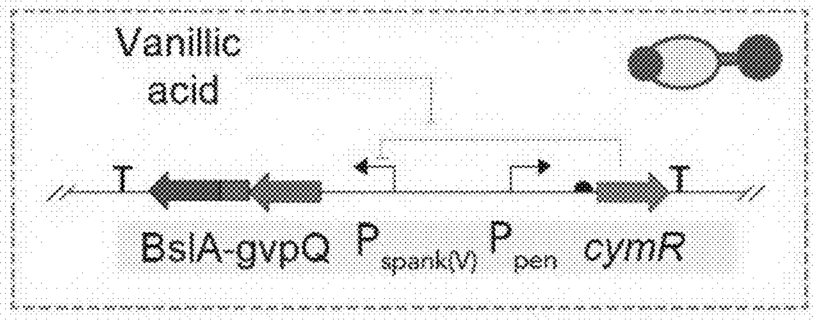
Figure 10C:
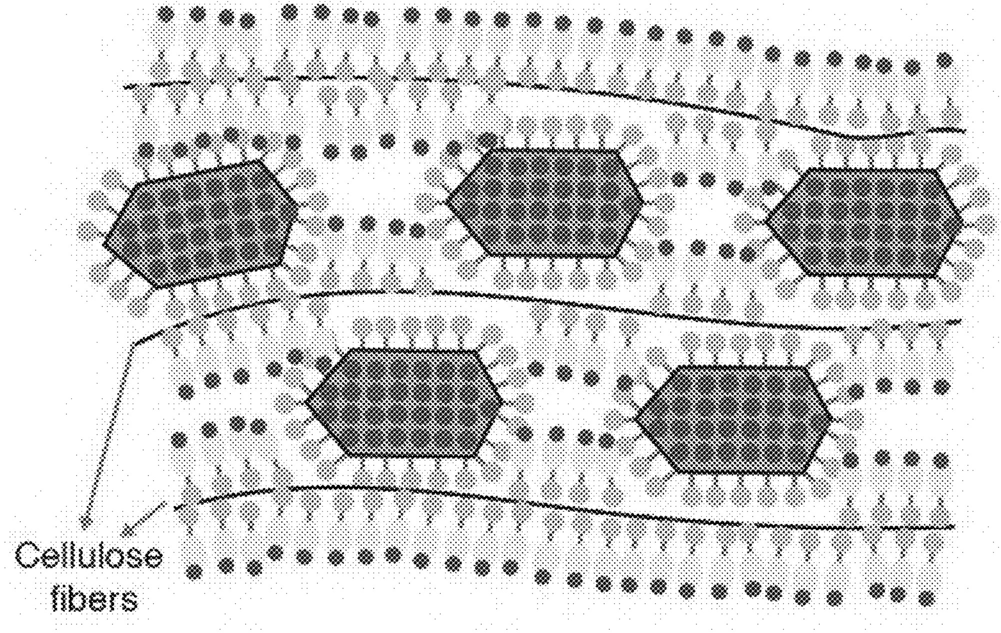

The addition of the gas vesicles to this material should significantly raise the R-value by reducing the solid portion and thus decreasing the heat transfer through the cellulose. To incorporate and secure the gas vesicle effectively within the cellulose network, genetic engineering tools can be used to link the C-terminus of the structural protein, GvpC or the equivalent, GvpQ, in the gas vesicles to a cellulose binding domain (CBD) or cellulose binding module (CBM) (FIG. 9). CBD are usually found in enzyme that required docking (for close proximity) in order to execute a function. Specific CBM family include the CBM47 and CBM48. Examples are CBM48 from *Komagataeibacter sucrofermentans* and *Micromonas pusilla*. For example, cellulase from *Trichoderma reesei* is an enzyme with a CBD linked via a peptide to a catalytic domain (CD). Adding CBD should allow anchoring of these gas vesicles to the cellulose fibers. A *B. subtilis* strain capable of producing these genetically modified gas vesicles can be manipulated to create bicone shaped vesicles (the initial step in their biogenesis of gas vesicles) to limit the size of these compartments for reduced convective heat transfer through the vesicles.

Another technical challenge is to modify the vesicles without compromising their structural integrity. By controlling the expression level of the gvpQ-CBD hybrid protein, the correct level of expression to maintain the structural integrity can be assayed. To prevent steric hindrance, misfolding and low protein yield and to effectively create this multidomain protein, various polypeptide linkers, (GSSGSS)n, (GSSSSS)n, (SSSSSS)n and (GGGGGG), can be placed between the GvpQ and CBD. To promote intermolecular reaction between the gas vesicles and the fibers, the length of the linkers can be varied (n=1-4). The shorter the linker the more hydrophobic as there are less hydrophilic moieties exposed, therefore when doing this assessment, the shorter ones may be best if binding is not compromised. The last step in the process is to collect the modified gas vesicles and incorporate them while growing the cellulose mat as in FIG. 9. To non-destructively inspect the size of the pores, X-ray computed tomography, typically used for examining gas holes in Swiss cheeses, can be used. This vesicles can be also inspected through SEM and TEM.

Test the R-Value of the Material.

To show feasibility the thermal conductivity of this hybrid material must be measured. For comparison, at room temperature vacuum has a thermal conductivity (λ) equals 0.001 W/mK and on the other side of the spectrum there is diamond with a λ=2000 W/mK. In building technology, the terms A is shown as a thermal resistance. This is denoted by R-value (British system units) or RSI (SI system units) which expresses the thickness of the sample divided by A. The higher the R-value the slower the rate of heat transfer through the insulation material. Using a heat flowmeter (Netzsch HFM 436 lambda), the thermal conductivity of the initial material (not processed) which is bare bacterial cellulose was measured as wet and dry sheets with A equal to 0.31 W/mK (comparable to soil) and 0.15 W/mK (comparable to dry plywood). The R-values equivalent for the wet and dry sheets are 0.46 and 0.93 $ft^{2\circ}$ F. h/Btu in one inch, respectively. For this material to be competitive, it should have an R-value/in circa R-6. This will make the material competitive with spray foam on top of adding the green and sustainability aspect. Below, and improved method is outlined.

Adding Holes to the Cellulose Materials to Increase the R-Value

A procedure to clean the cellulose, remove the cells, and dry it was implemented. The R-value of the resulting material with two different treatments was measured. The first sample was simply a rectangular sample of several stacked layers of the cleaned cellulose.

For the second treatment holes (diameter ~2 mm) were punched in sheets of the material using a custom-built device for high throughput. The printed device consists of a 3D printed 8"×6" holder for multiple push-pins spaced about ⅕ inch (5 mm) apart. Each sheet was punched multiple times in different orientations to create hundreds of “randomly” arranged holes. The last step of making this sample consisted of stacking rectangular cutouts of the sheets so that the holes did not line up in different layers.

The measured R-value for Sample 1 (simple stacking) was 1.78. The measure R-value for Sample 2 (layers with holes) was 3.27, which is nearly as high the R-value of fiberglass insulation, which is about 3.5. By adding the GVs, materials with even higher values (with nanopore sized) can be produced. Furthermore, as a risk mitigation strategy, optimizing the size and arrangement of punched holes in multiple layers could lead to a cost competitive material with high R-value even without the addition of gas vesicles as these materials are green.

Adding a cocktail of protease inhibitors would prevent GVs from getting degraded by *G. xylinus* proteases before getting incorporated and shaping the cellulose mat. The GVs after purification and resuspension in 1×PBS are mixed with 2X SCOBY media in a 1:1 ratio with the inoculum of *G. xylinus* cells grown for 3 days (when using the WT strain). The mixture of the WT cells, media and GVs are grown for 8 days on square plates. After this the mat is cleaned with 2.5% NaOH and bleach before folding over multiple times. Other scaffolding material could be used in the process especially grown material such as mycelium cells. Other scaffolding materials include silk, down, leather, fur, wool, polyester, polyhydroxyalkanoates (PHAs) and silica. A linker module needs to be present to promote attachment of these scaffolding materials to the GVs.

Part #3: Genetically Engineering Hydrophobicity and Fire-Retardant Properties into the Fibers.

Making the Cellulose Fibers Hydrophobic by Coating the Fibers with CBD-Hydrophobin.

For this material to be a multifunctional insulation material, its hydrophobicity or vapor barrier capability must be confirmed. Keeping a wall sections dry is a critical property of any building insulation material to prevent the growth of mold. If the addition of the gas vesicles does not provide sufficient vapor barrier performance, modification of the vesicles' coating through genetic engineering will be needed. This modification might need to be done only on the surface of the material and not within the material. A candidate with a hydrophobic cap is the protein, BslA, which would mask the small hydrophilic protein, GvpQ on a gas vesicle. The BslA proteins forms an elastic film in an air-water interphase.

In addition to covering the gas vesicles, it is helpful to cloak the hydrophilic cellulose fibers. A genetic circuit has been designed to do this using the same BslA protein (FIG. 11). Other hydrophobins can be screened to find the right candidate suited for this application. The candidates hydrophobins include HFBI, EAS, DewA, chaplins, SapB, SapT, cryparin and HypA.

*B. subtilis* is known for its ability to secrete large quantities of protein (20-25 g/L have been reported) and has been used widely in industry. Considering this, *B. subtilis* can be used as a workhorse for producing and secreting out this coating enzyme. Enzymes targeted for secretion contain a signaling peptide (SP), and are translocated to the secretion machinery. Once the surface has been modified with these engineered proteins, they can be tested using contact angle measurements. A contact angle greater than 120° would make this material fall in the hydrophobic range. This measurement can be done through using an optical tensiometer device.

Modify the Fibers to be Fire-Resistant with Melanin Materials

Untreated cellulose with high porosity is a potential fire hazard. To comply with building fire codes, treatment of our material with boric acid, halogenated anilines, or brominated compounds (BRFs) would bring it into compliance with building fire codes. However, to avoid or reduce these environmentally problematic treatments, bacterial produced melanin to enhance the flame-retardant properties of our materials can be explored. Melanin resembles synthetic polydopamine, which other researchers have shown to be useful as a fire retardant. A tyrosinase enzyme can be expressed to form melanin in *B. subtilis* and create a composite polymeric material of cellulose and melanin at the surface of the material as a protective layer. Testing can determine if this composite material will char, sequester free radicals, and consequently stop the spread of fire.

Conclusions:

It is expected that the degree of entanglement and packing density is important, as the nanoporosity of the network is important to obtaining a material with a high R-value. The cellulose network will act as a carrier for the interweaved gas vesicles which brings about the nanoscale porosity to the network. At the cellulose-medium interfaces the hydrophobins, BslA or HFBI could impart the hydrophobicity properties needed to keep this material from getting wet (antimicrobial properties) and to preserve the insulation properties. In addition to moving genes to another more suitable chassis, genetically engineering tools are useful because instead of adding expensive chemicals for surface modification (e.g. adding hydrophobicity), those changes can be introduced at the genetic level. In the future, the capabilities of gas vesicle to dampen sound due to the ability of gas vesicles to scatter sound waves and other applications for this cutting-edge research can be explored. These applications encompass hydrophobic clothing and thin lining for coats and vehicles (transportation), oil spills cleanups, cosmetics, acoustic insulation, filtration, packaging materials and thermal shielding for extreme cold and hot environments (deep ocean, artic and space explorations).

Optimized Media and Growth Conditions to Efficiently Grow its Main Cellulose Producer.

Figures 11A, 11B, 11C, 11D, 11E, 11F, 11G, 11H:
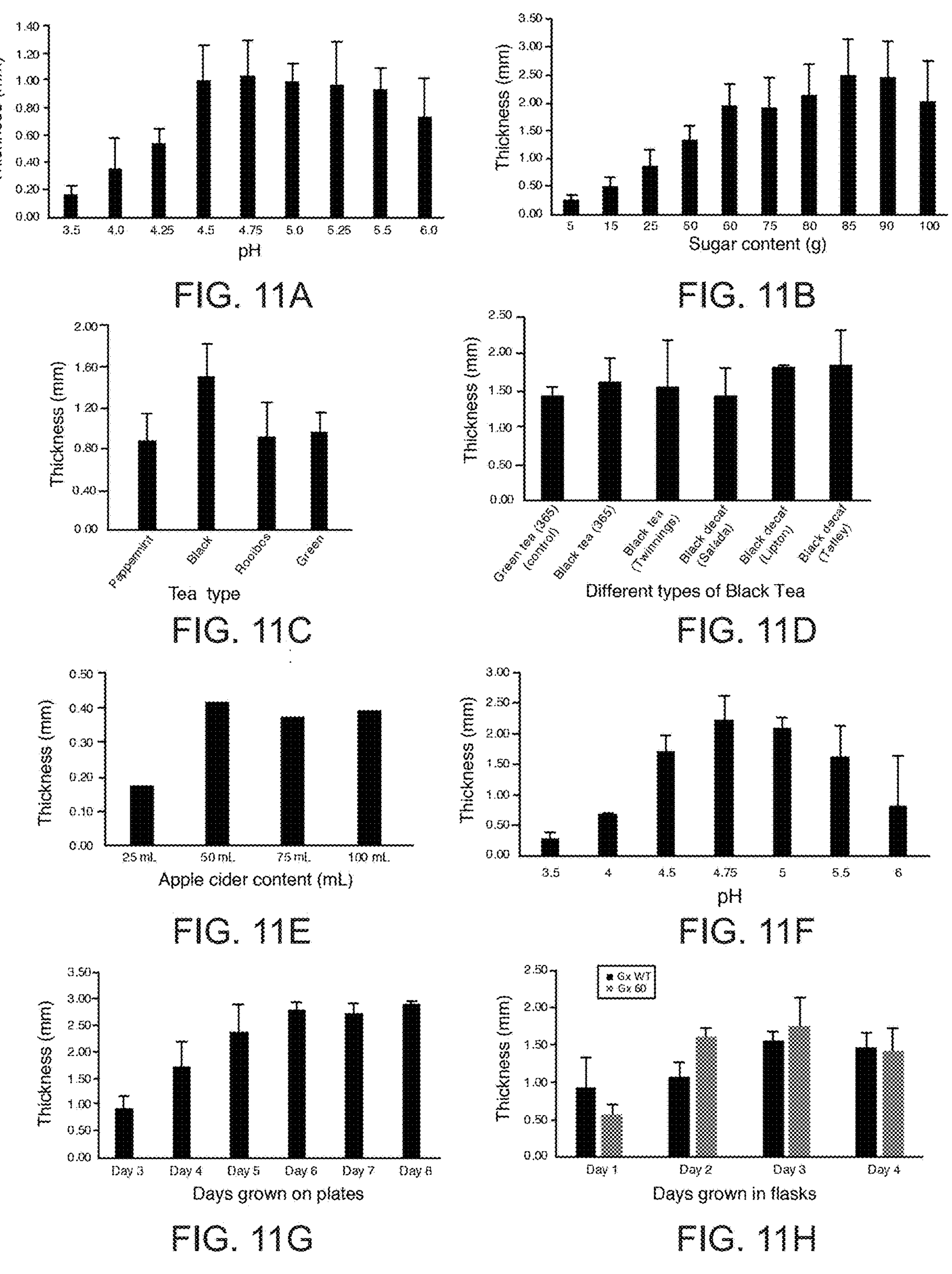
FIGS. 11A-11H. Optimization media for best growth conditions reported in terms of thickness of mat. Optimization of the media in terms of FIG. 11A: pH level FIG. 11B.

Media preparation. To make the media the following components are combined: 800 mL of deionized water, 85 g of sugar (any refined sugar works), 1 teabag of Black tea and 100 mL of apple cider vinegar. The pH is adjusted with NaOH. The sugar is dissolved in the water by shaking vigorously before adding the teabag as this can break in the process. This media has been optimized to grow *Gluconacetobacter xylinus* by adjusting the pH content. The pH should be 4.75 for best results (see FIG. 11A). The media is then autoclaved for 30 min. FIG. 11 also shows the optimization of sugar, type of tea, apple cider vinegar (and after adjusting the pH). We tested the time that the wild type cells need to be grown before the growth plateaus which is about 6 days for WT cells, as shown in FIG. 11G.

Figure 12C:
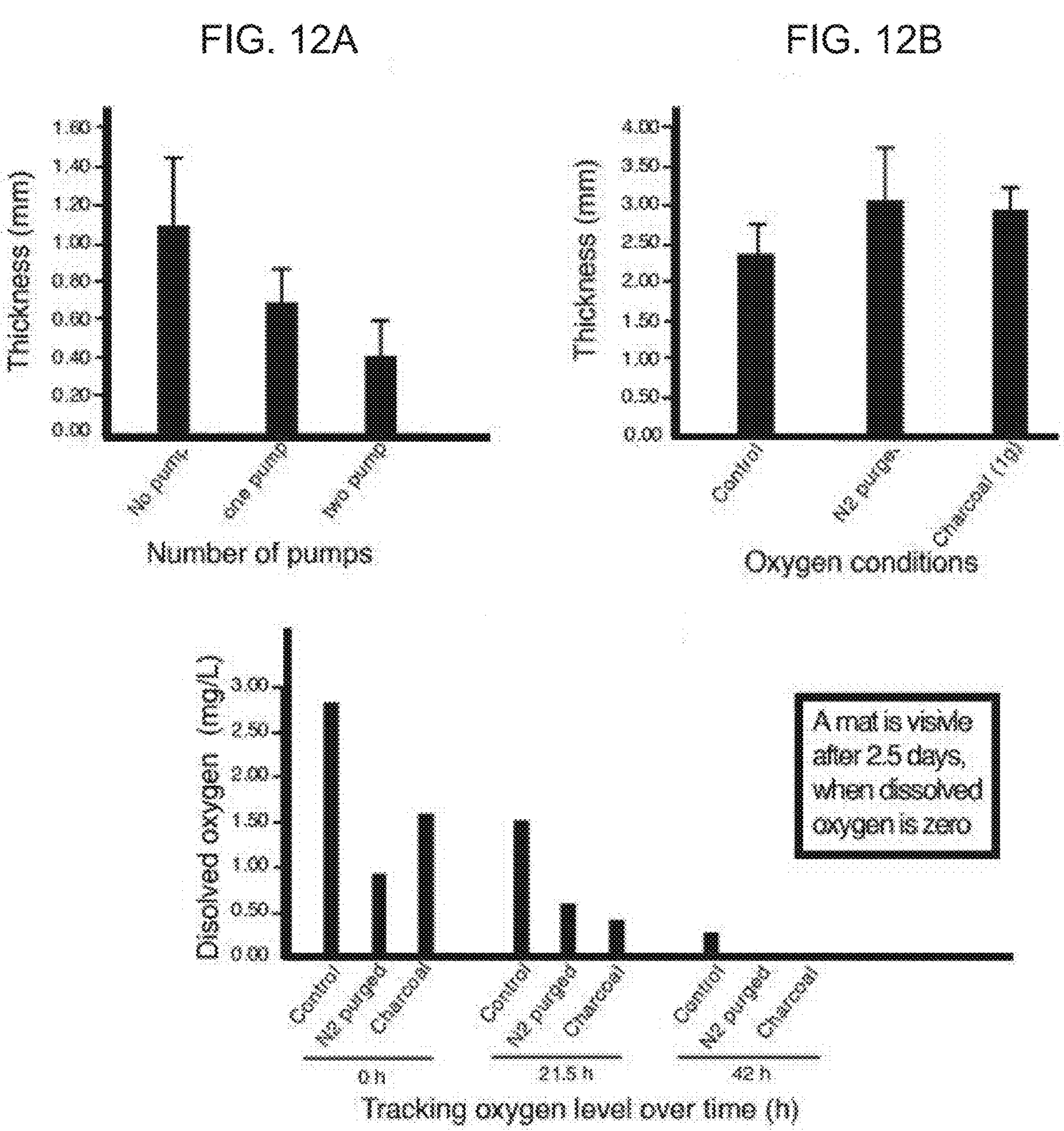

We tested the effect of oxygen in the growth of the mat. First, we set-up zero, one and two pumps pumping air (not pure oxygen) into the tray while the cells grew (FIG. 12A). Having two pumps resulted in the weakest and thinnest mat (FIG. 12A). The cells are growing, but not on the surface where we harvest the mat from. The cellulose mat appears at the air-water interface when the dissolved oxygen in the media drops to zero (FIG. 12C). The cells need oxygen to grow so our conclusion is that the cells are growing at the air-water interphase because the oxygen is highest at this point when the dissolved oxygen is zero in the bulk of the liquid. Another experiment that corroborates this conclusion is using airtight lids. Cells did not grow as well in these airtight containers presumably because of insufficient oxygen in the air gap. We show that purging the media with nitrogen gas for about 10 min (5 psi) or adding charcoal (~1 g) to the media helps with obtaining a thicker mat at the air-water interphase (FIG. 12B). These two methods exacerbated the displacement of dissolved oxygen from the media thus promoting growth at the air-water interface. Using charcoal might not be the best approach as it complicates the cleaning of the mat in downstream steps.

Figures 13A, 13B, 13C, 13D:
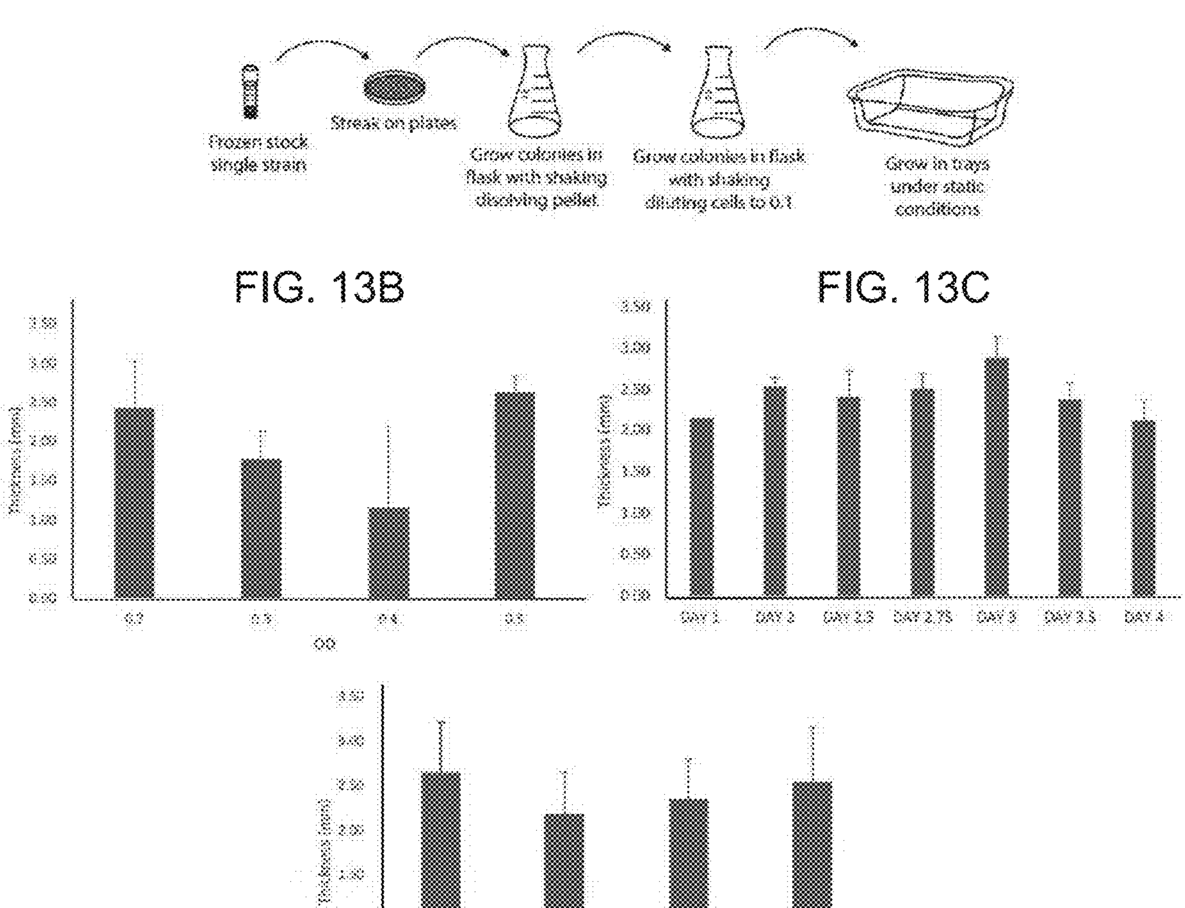
FIGS. 13A-13D. Optimizing cell concentration at each step.

Initial culture. In FIG. 13A, we show the whole process of growing the mat from the glycerol stock to the static culture. We streak *G. xylinus* wild-type on HS/agar plates from frozen stock and let grow for about 2.5 days. We prepared HS medium (typically 1 L). The rest can be stored for later use. We introduced a single string of colonies of *G. xylinus* to the liquid HS medium (25 mL volume in the 125 mL flasks) and 0.1% cellulase (1% cellulase filter sterilized and stored at 4° C.). The cellulase helps dissolved the cellulose for getting a reliable/consistent and accurate optical density (OD600) for the back dilution in the next step. The cells are allowed to grow in incubator at 30° C. with shaking (100 rpm) for ~2 days. The result is a light turbid suspension of bacteria.

Preparation of consistent inoculum for the static growth. We measured the $OD_{600}$ of the initial culture with a spectrophotometer. The cells are diluted back to an $OD_{600}$ of 0.1 in 25 mL of HS media (adjusting the pH to 4.5) in a 125 mL Erlenmeyer flask. The cells are then grown at 30° C. for an additional 2 days. This time we omitted adding cellulase and the result is a suspension of pellets averaging 0.5-2 mm diameter. These cells can be spread out evenly in the next step to obtain a uniform mat on the rectangular dishes. If cellulase is not added in the earlier step, then lumps of cells/cellulose of various sizes are obtained and uneven/no uniform mat is the result.

Static Culture. For the static culture, we add 300 mL of the SCOBY media to the rectangular Pyrex dish and add the whole 25 mL of the inoculum culture. We cover each dish with aluminum foil and pinch sealed. We make sure the foil is not sagging or touching the media. We then place dishes in static incubator at 30° C. for 6 days (see FIG. 11G). The product is a layer of bacterial cellulose at the air-medium interface.

Processing of the material. We remove the cellulose layer from culture dish. Then rinse cellulose layer with 10% bleach. Soak cellulose layer in 2% NaOH solution at RT. We then rinse the cellulose layer with distilled water 3 times and soaked cellulose layer in 20% bleach at ambient temperature for 2 hours. This step is repeated if light brown spots are still visible. We then rinse the mat at least twice and then we submerged cellulose layers in 1% glycerol at ambient temperature for 24 hours. We then dried cellulose layer in oven at 60° C. for 3 hours. Alternatively, we can dry a mat at room temperature for 24 hours. To fix the sugars in the mat, we add a proprietary component.

The product is a dry, thin, flexible synthetic cellulose sheet suitable for layering. A single sheet resembles plastics and as a lamination of layers resemble a leather material. The material can also serve as a backing material for other vegan or leather products. Beside *G. xylinus*, the above process media composition can also work in other highly cellulose prolific organism such as *Komagataeibacter rhaeticus* and *Komagataeibacter hasenii*.

In FIG. 13A, we show the steps we take to grow these cells in mats. We investigated the ideal optical density to inoculate the cells in the second flask step (FIG. 13B). We sampled cells from the HS+cellulase steps (first flask) at different $OD_{600}$ before transferring to the second flask with HS (no cellulase) at OD=0.1. For all of the samples, we grew cells in second flask for three days. We obtained the best results with $OD_{600}$=0.2 and $OD_{600}$=0.5 (FIG. 13B). In the next step, harvesting cells at OD=0.2 in the first flask, we determined the ideal time to grow the cells in the second flask for the small dishes (FIG. 13C) and larger trays (FIG. 13D) and still diluting back to 0.1 in the second flask. For the small dishes, it was 3 days and for the big trays it was 2 days.

Next, we determined if removing the cellulase in the second flask before moving to the static growth would help with obtaining a thicker mat and it did.

Figures 14A, 14B, 14C, 14D:
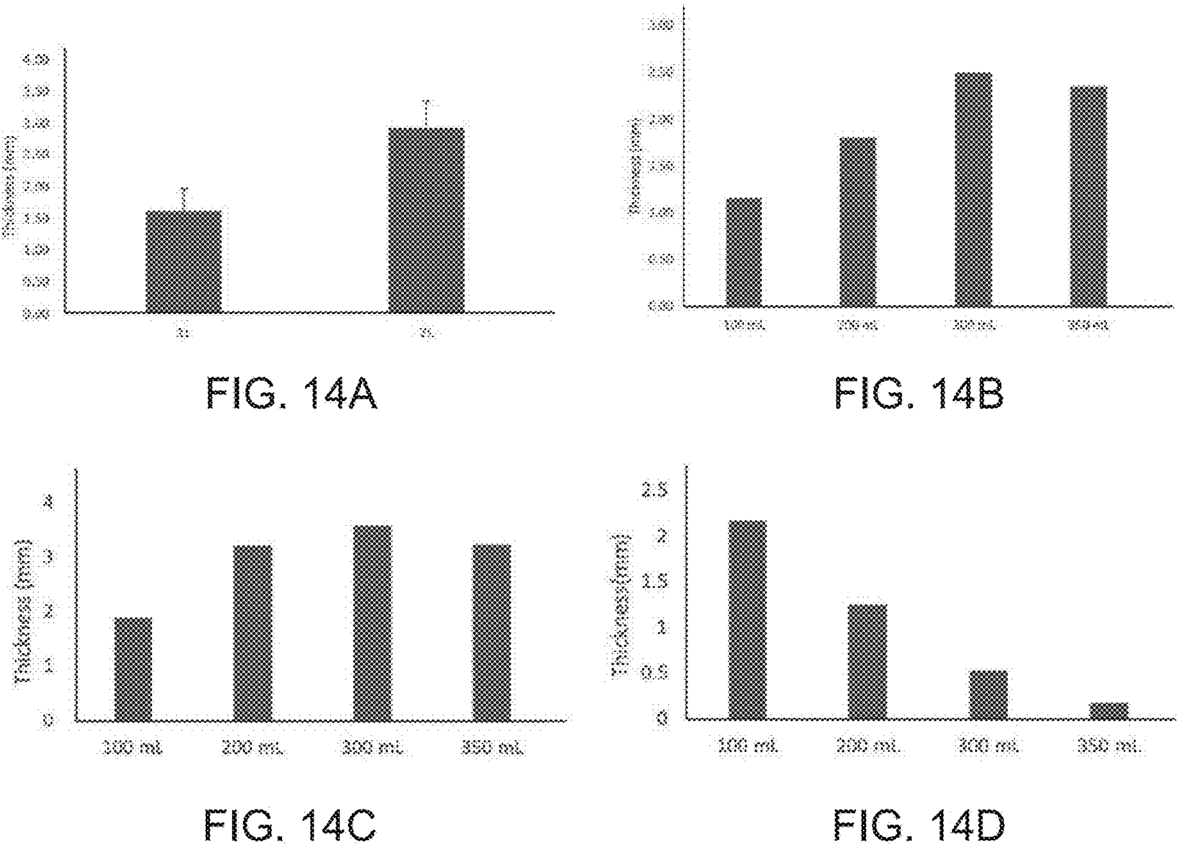
FIGS. 14A-14D. Examining water and sugar content.

One concern in growing these cells is the amount of water required for the static growth. The water can be recycled in the process but decreasing the amount of water needed would reduce resource demand. We examined if using a higher concentration in the media would create a thicker material and help conserve some water (FIG. 14).

Improve Thermal Insulative Properties with Gas Vesicles (GVs) and Cellulose

To produce an aerogel with GVs and bacterial cellulose, we explored several approaches as follows: With only cellulose using a physical method to introduce holes using an array of pins; Drying the material with a critical point dryer to preserve the porosity of the material; Embedding GVs (from a natural producer) in agar and agarose samples; Soaking GVs (from a natural producer) in cellulose and drying; Embedding GVs (from a natural producer) in cellulose as they grow; Reducing the surface tension by including hydrophobins; and Using lyophilization We engineered cells to produce gas vesicles. To test whether gas vesicles are suitable for making an aerogel, we opted for using a natural producer specifically *Halobacterium salinarum*. At the same time, we were making an engineered strain, that we can manipulate genetically to bind other molecules and make them functional. We also decided to explore other physical and chemical methods without using gas vesicles to make our cellulose an aerogels. These methods can have an economical advantage as they do not require growing a second organism.

Pin array. After we processed our material removing the cells in the cellulose network, we dried the individual layer and used an array of pin to poke the holes. After aligning the layers, we obtained a material with a decent thermal conductivity. The thermal conductivity of the control sample without holes was 0.081 W/mK, and the one with holes was 0.044 W/mK, confirming the effectiveness of this method.

Critical point drying samples. We made cellulose material into an insulator by growing the cells in SCOBY media. We used the WT and our engineering strain GX 60. Using a die cutter that is a 1" diameter, we obtained a disc that can be loaded and measure with our C-therm Trident instrument. We then treated the material with 1% NaOH for 1 hour, 20% bleach for 1 hour, then another 20% bleach for another hour. We rinsed at least 3 times with copious amount of water. We exchanged the water by submerging the material in 25% ethanol, then 50% ethanol and 75% ethanol for 1 hour each. The final exchange was done in 100% ethanol (dehydrated with molecular sieves) overnight with shaking. The removal of water allows miscibility with liquid $CO_2$. Using an Autosamdry-815 Critical point dryer (tousimis) and respective holder, the samples were supercritical dried by first filling the chamber with liquid $CO_2$ allowing the pressure and temperature to go past the critical point (31.1° C., 1072 psi) in a phase diagram. The purge timer dial was set at 4. After measuring with a C-therm Trident, MTPS sensor, the material thermal conductivity was 0.0355 W/mK for the wild-type and 0.0365 W/mK for the engineered strain. When the WT sample was completely dried, the thermal conductivity was as low as 0.031 W/mK. This thermal conductivity is on par with polyurethane spray foam (0.03 W/mK), Styrofoam (0.033 W/mK) and extruded polystyrene (0.03) W/mK. The dry sample has the same feel as Styrofoam. We obtained similar results by drying the samples with a lyophilizer. The k value was 0.0339 W/mK. The water in these samples was also exchange for ethanol.

Figure 15A:
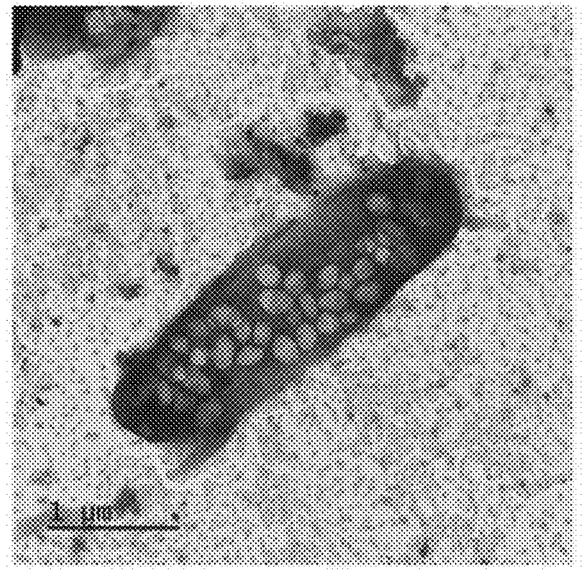
FIGS. 15A-15B.
Figure 15B:
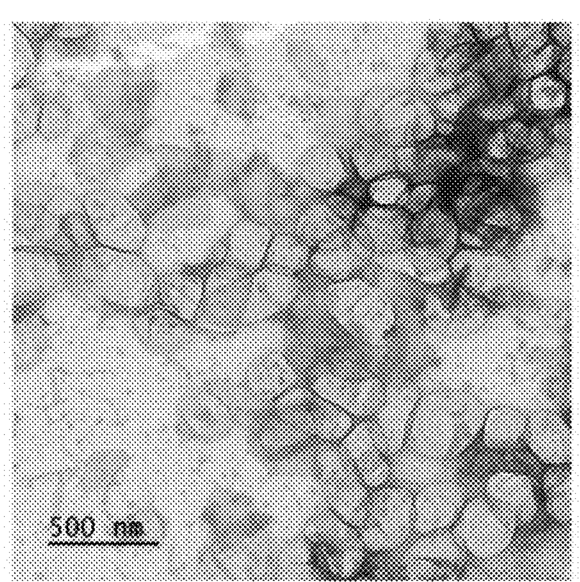

Preparing GVs and using them to improve insulative properties. We decided to use GVs from *H. salinarum* to test our hypothesis that using gas vesicles could improve the insulative properties of hydrogels. These cells grow in a high salt media which facilitates growth by reducing chances of contamination. As we purified the GVs from these cells, we realized we needed to grow a lot of cells to obtain enough GVs. We used separatory funnels to separate and concentrate the cells by buoyancy. Separation takes about six days. We 3D printed holders for 50 mL and 2.0 mL tubes designed for our floor centrifuge rotor to spin everything at once and expedite the purification process. The GVs tend to stick to the side of the plastic tubes. After collecting the buoyant cells and lysing and purifying them, we inspect these gas vesicles with TEM (FIGS. 15A and B). We generate a growth curve of these cells using our spectrophotometer.

Figures 16A, 16B, 16C:
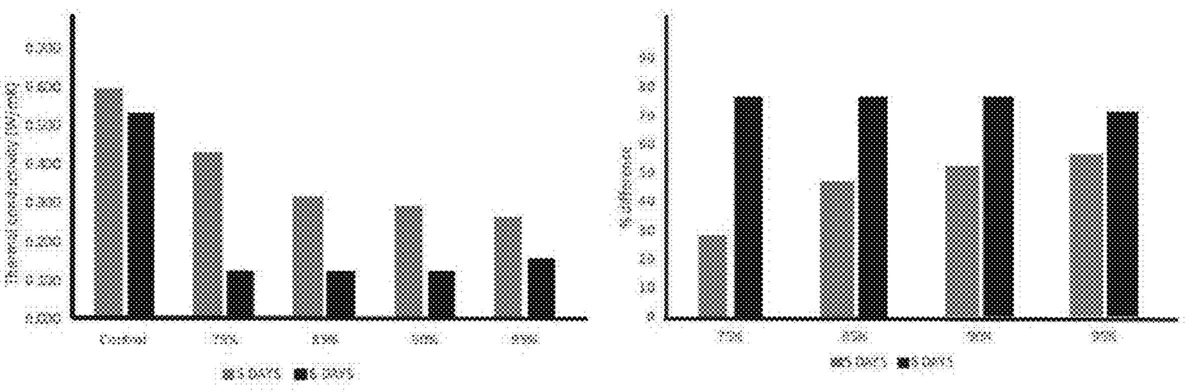
FIGS. 16A-16C. Embedding GVs in agar and agarose polymer

We found that the higher the percentage of GVs the higher the difference in the thermal conductivity, and it is more pronounced after drying the samples in a fridge and getting rid of as much of the water as possible. The polymers used in this experiment were agar (FIG. 16A) and agarose (FIGS. 16B and C). The GVs concentration has to be OD600>3 to see a significant difference. The material is then dried at 4° C. for a couple of days. When the material is dried at room temperature, we observe bigger holes in the sample, possibly from collapsing GVs. One way to improve this method is to reinforce the GVs or to use GVs that can withstand higher pressures and preserve the structure as water evaporates. At first, we only tried GV concentration up to 85% (FIG. 16A), because we were microwaving the hydrogel solution (0.5% final) and adding the GV solution to it. Microwaving the GVs causes them to collapse immediately. We decided to switch the preparation method and heat up the GVs solution while using a low melting temperature agarose (65° C.). We heated the solutions up to 65° C., and this allowed increasing the GVs concentration to 95%. For FIG. 16B, we took the average of the thermal conductivity at different spots in the 60 mm petri dishes. FIG. 16C shows the percent difference of using different GVs percentage in comparison with the control having only water.

In addition to embedding the GVs in agar and agarose, we also soaked processed cellulose mats in the concentrated GVs solution, layered them and let it dry for a couple of days before measuring the thermal conductivity using the C-therm Trident. With this method, we measured the thermal conductivity to be 0.0612 W/mK for the dried mats and 0.0548 W/mK using the mat that have not been dried. We measured the thermal conductivity of the powder form of GV (a dried paste) to be 0.077 W/mK. The thermal conductivity of the samples increases with subsequent measurements, probably because heat pulses from the measuring instrument damage the samples.

Figures 17A, 17B, 17C, 17D:
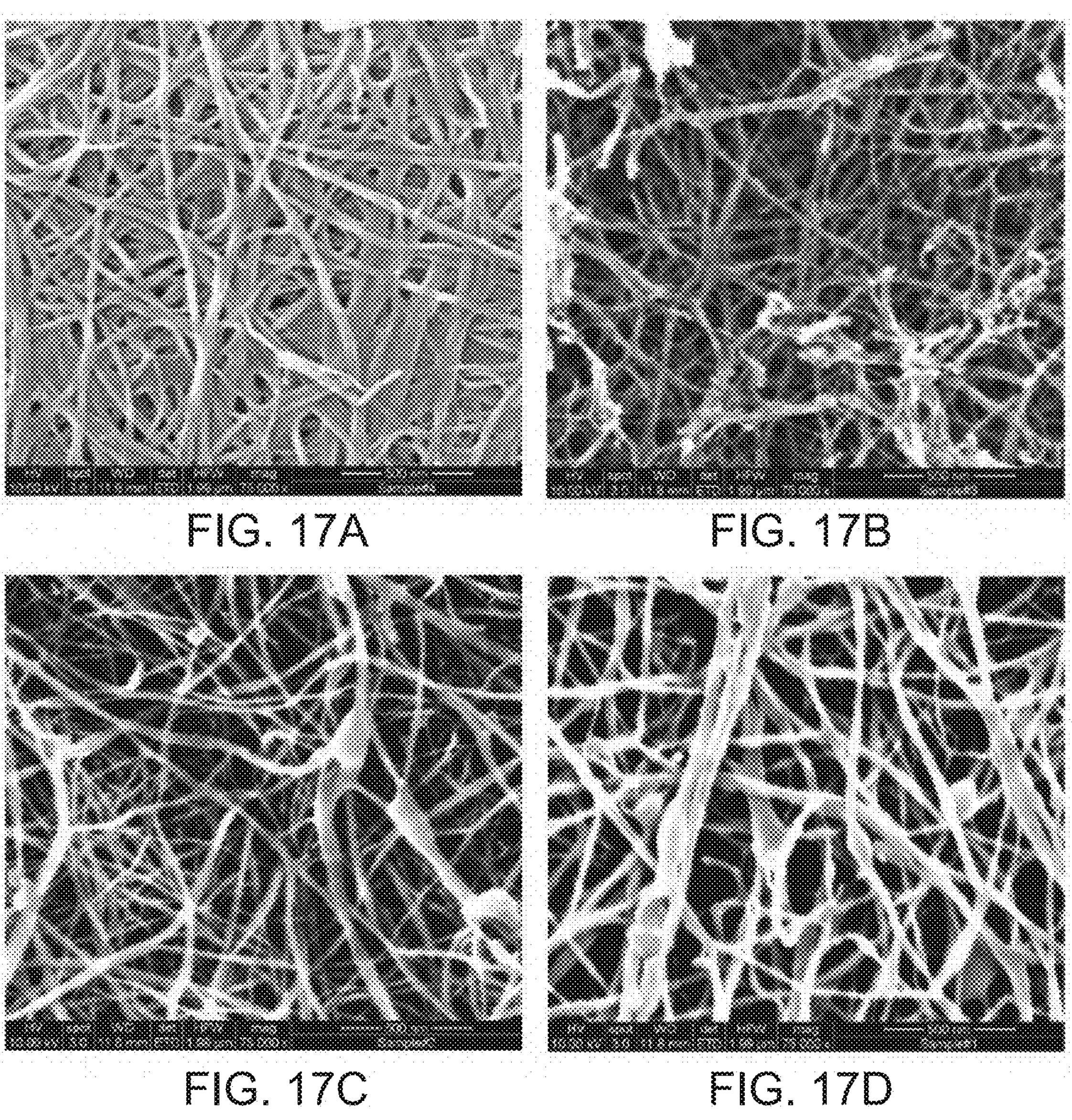
FIGS. 17A-17D. Embedding GVs while growing the cellulose mat.

Embedded GVs in the cellulose network. The last method attempted was growing the cellulose mat in a bath of concentrated GVs. We prepared a concentrated solution of the media (5X SCOBY) to dilute it to 1X using the GVs solution. We set up the samples so that samples contained 25%, 50% and 75% GVs. The control sample has no GVs in it. We obtained the opposite results of what we were expecting. With the 75% GVs, we obtained the worse results. The thermal conductivity for the WT, 25%, 50% and 75% were 0.0299, 0.0303, 0.0318 and 0.0339 W/mK, respectively. FIG. 17 shows the SEM micrographs for each sample. Our hypothesis is that the cells might need more water to make the cellulose mats as the sample with a high percentage of GVs have much less water. The GVs might be clumping and preventing the growth of the cellulose network. Since the mat grows at the top and pushes the mat downward, spraying the GVs on the mat as they grow engulfing them is a better approach. It also saves on the quantity of GVs needed for the process. This way we can maintain the water and nutrients needed for forming the network. That is, allow the cells to grow the network continuously while also embedding the gas vesicles. The gas vesicles act as the molds for the network.

Created Genetically Engineering Cells to Produce Gas Vesicles (GVs)

To engineer the gas vesicle system to integrate other modules and impart properties on the surface of these nanostructures, we must manipulate the genes involved in the formation of these structures. The goal is to add a cellulose binding domain (CBD) to the surface of these structures to facilitate attachment to the cellulose scaffold. We decided to focus on the gene cluster that encodes production of gas vesicles from *Bacillus megaterium* because of its smaller size of 7 kb compared to the other gyp gene clusters.

We took two approaches to building this modular (modifiable) genetic system. First, we took the natural system, as is, with its natural promoter and Ribosome Binding Sites (RBSs), and placed it in a vector capable of replicating in *Bacillus subtilis*. Second, we used an inducible promoter (IPTG) and ensured that every gene in the cluster was turned on by including a *B. subtilis* 's RBS.

Figures 18A, 18B, 18C, 18D, 18E:
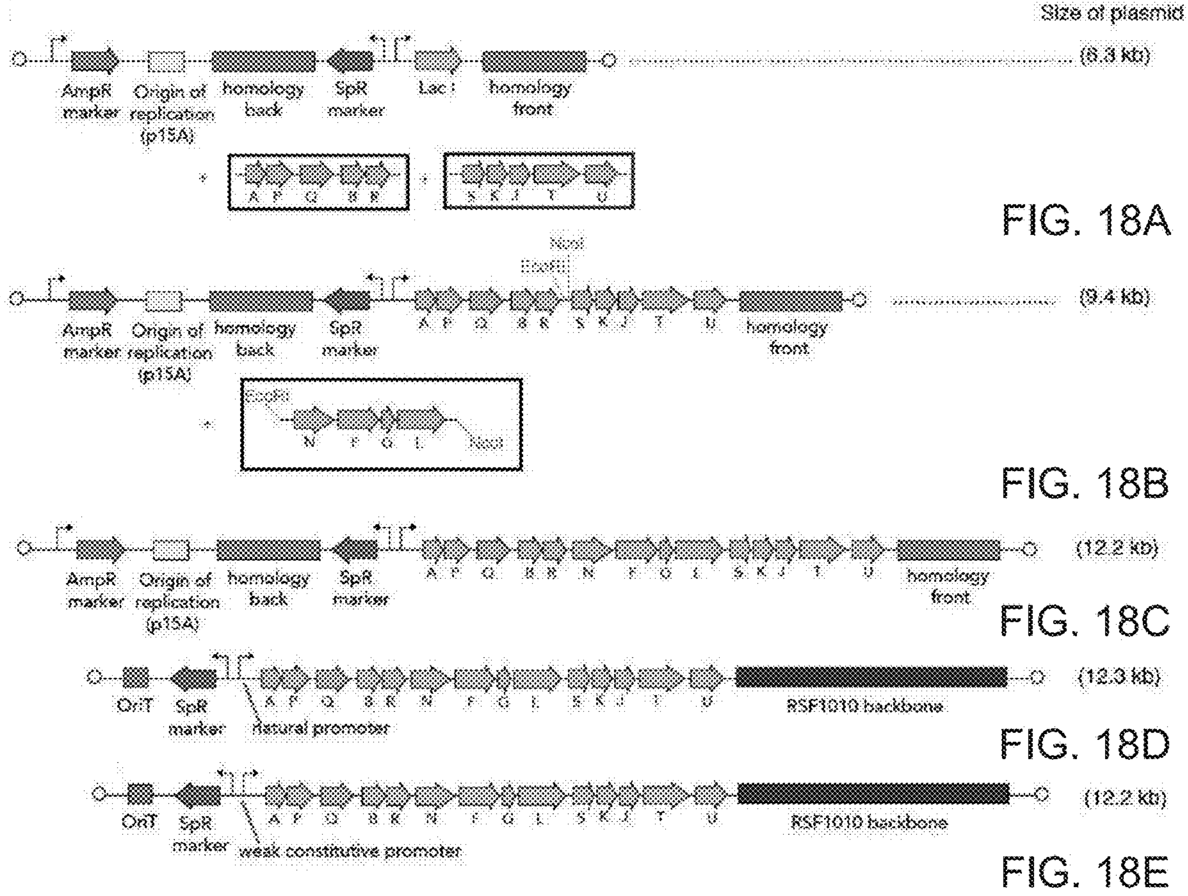
FIGS. 18A-18E. Gene circuit with gas vesicle gene cluster from *Bacillus megaterium* using natural promoter and RBSs. This shows the steps in building the plasmid using gene fragments.

To begin, we built a backbone plasmid with the gene fragments that we ordered from Azenta. We chose to start using COLE1 origin to express the GV cluster, but the system kept breaking in the cloning procedure (no colonies on plates). Therefore, we moved the circuit to a lower copy plasmid with the p15A origin (plasmid 450 #11 in FIG. 18*a*). To this backbone, we added the parts with the natural RBSs and promoter to create plasmid 451 #6 in FIG. 18*b*. At first, we attempted to add all the parts of the gyp gene cluster, but the cloning did not work. We decided to clone it in chunks to facilitate the cloning process. We first added genes APQBR and SKJTU using golden gate. Within these parts we added enzyme NcoI and EcoRI to clone in the last set of genes NFGL to create plasmid 457 #8 (FIG. 18*c*). We had a couple of mutations in plasmid 457 #8 so we built plasmid 492 #28 and 492 #31 (FIG. 18*d*) on a broad host lower copy vector with the natural promoter from *B. megaterium* (with an RSF1010 origin).

Figures 19A, 19B:
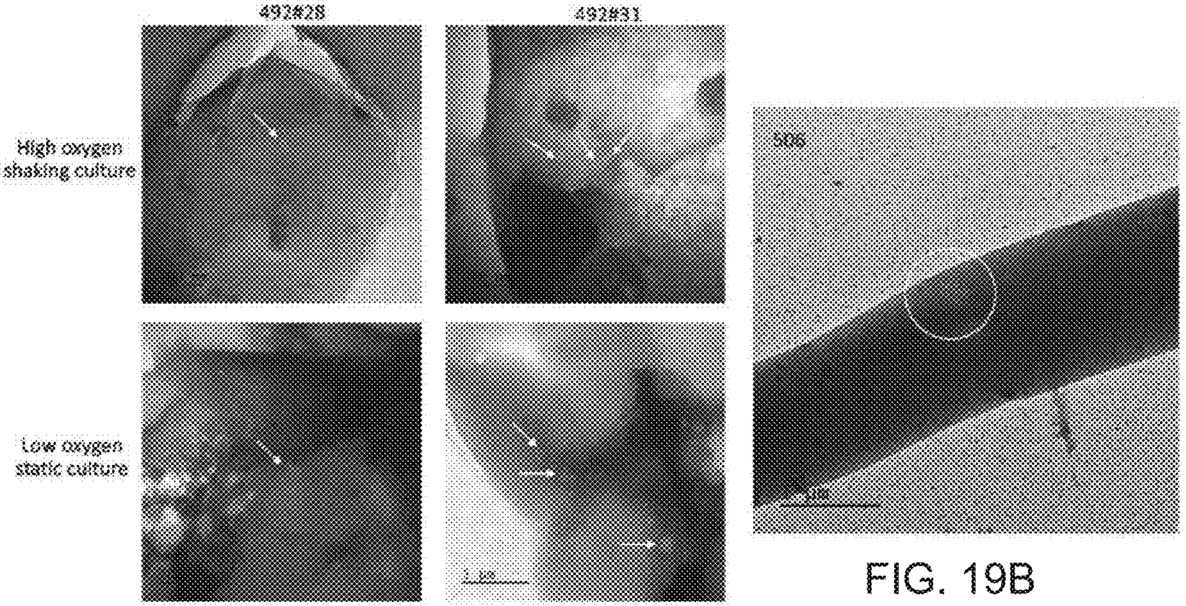
FIGS. 19A-19B. TEM results.

Through TEM microscopy, we examined the GVs produced by these cells (FIG. 19*a*). We spotted a few gas vesicles while growing these cells under normal aerated conditions. It is unknown what turns on this particular promoter on, and so we grew the cells under low oxygen conditions. As shown in FIG. 19*a*, we were able to see more GVs in the TEM images of cell grown with low oxygen conditions. We also took this same system and placed a constitute weak promoter (PJ23114) to create 506 #5 (FIG. 18*e*). FIG. 19*b* shows a representative image of these cells. We attempted using stronger promoters, but we were not able to clone them perhaps due too toxic to the cells.

Figures 20A, 20B, 20C, 20D, 20E:
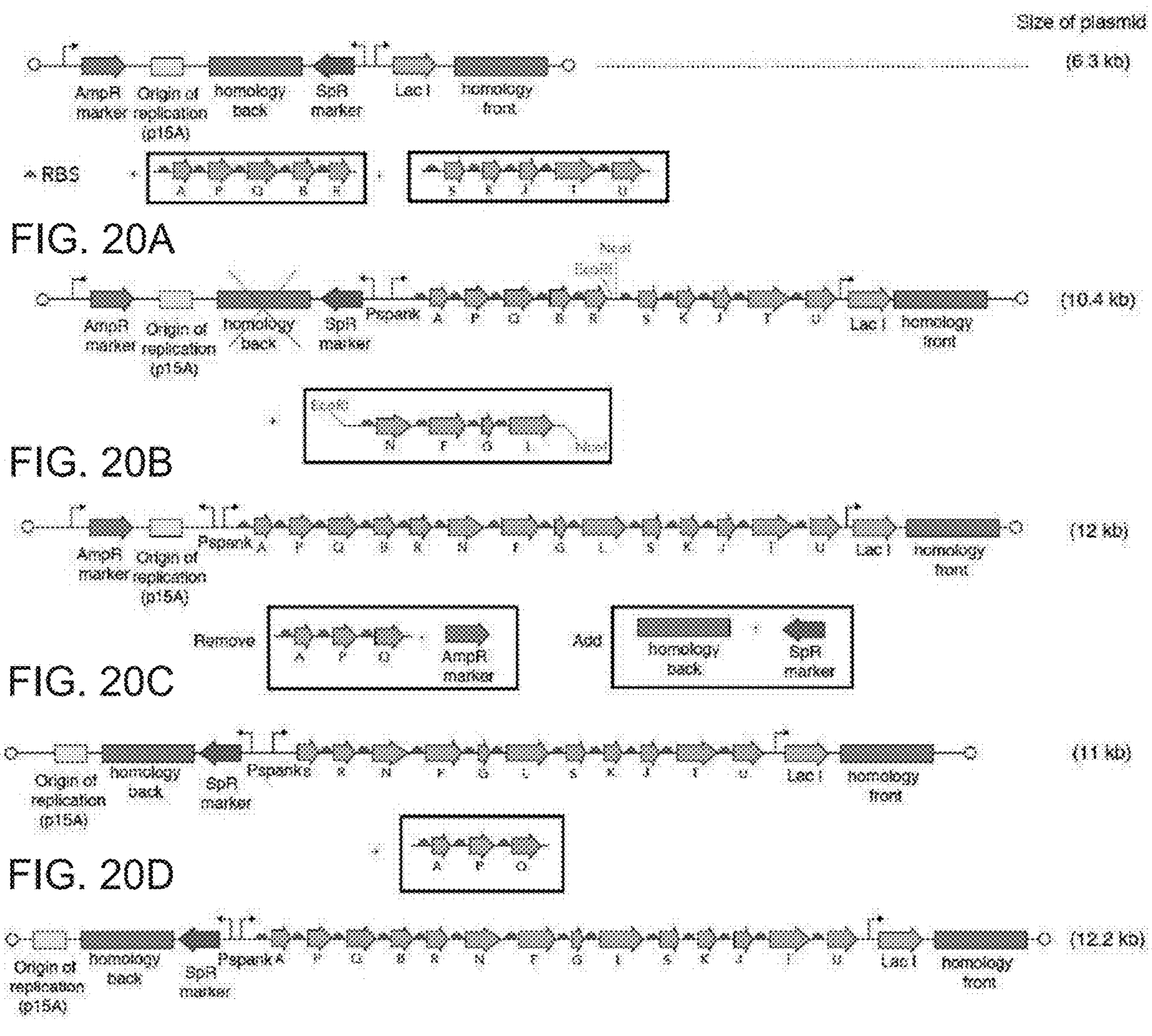
FIGS. 20A-20E. Gene circuit with gas vesicle gene cluster from *Bacillus megaterium* using the $P_{spank}$ IPTG inducible promoter and the SpoVG RBSs. This shows the steps in building the plasmid using gene fragments.
Figure 21A:
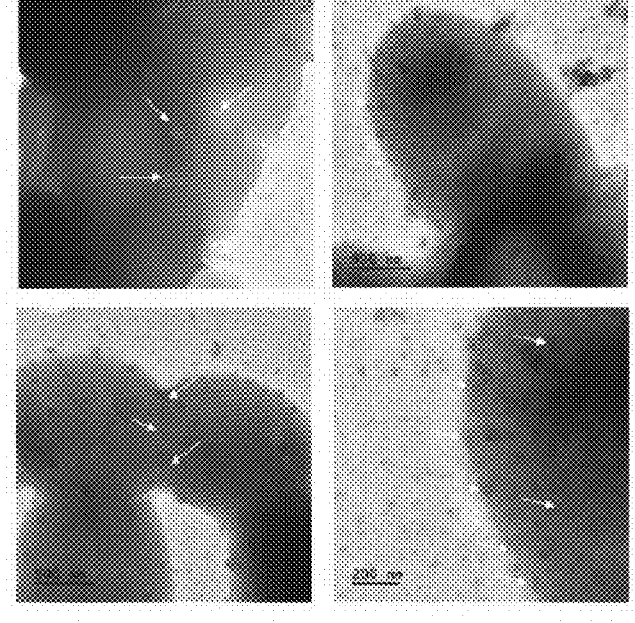
FIGS. 21A-21B. Engineered cells to produce gas vesicles changing promoter and RBSs.
Figure 21B:
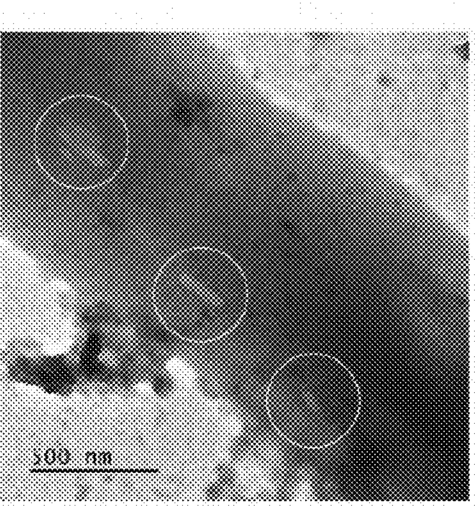
Figure 22:
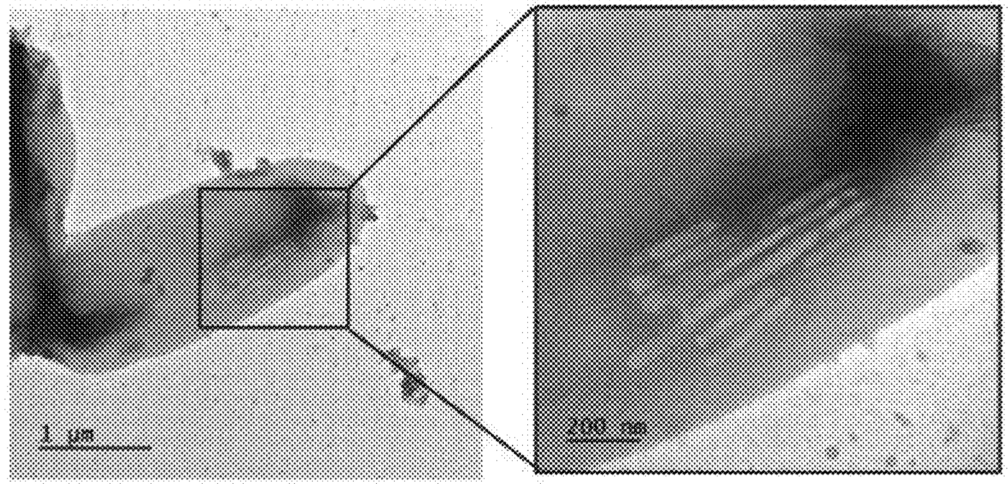
FIG. 22. Engineered cells to produce gas vesicles optimizing conditions such as inducer concentration, induction time and time of growth (FIG. 20 shows the 505 #13 gene circuits corresponding to these cells).

We also built a plasmid with an inducible system and ensured every gene was turned on in the final *B. subtilis* strain by replacing the natural RBS with the spoVG RBSs. FIG. 20 shows the cloning steps taken to build 467 #13 (FIG. 20*d*) and 505 #13 (FIG. 20*e*). Plasmid 467 #13 lacks the first three genes in the cluster, and it is still functional. These plasmids were more difficult to clone than the one with natural RBS and promoter. FIGS. 21 and 22 show the TEM results. Temperature made a striking difference in the growth of GVs. To produce larger GVs the cells need to grow at 30°

C. (FIG. 21*b*). At 37° C. smaller GVs are observed at the surface of the cells (FIG. 21*a*). The small vesicles positioning within the cells' membrane raises the question of how these gasses get into the cells. This observed feature may be the initial step in the GV formation.

To see the GVs, we needed to optimize the protocol to make protoplasts as the GVs are not visible without removing the outer membrane. We optimized the protocol to observe these GVs. FIG. 22 shows the results after optimizing a couple of parameters such as induction time, inducer concentration, and time of growth to produce more GVs.

Identified Attachment Site for Doing Chemistry on the Surface of the GVs.

To attach modulus to the surface of the GVs, we needed to determine which are the surface protein in the *B. megaterium* cluster. We had two candidates (gvpP and gvpQ) that could be the equivalent of gvpC (a surface protein that strengthen GVs) as they followed gvpA as in the gyp gene cluster of other organisms. We created fusion protein with these genes using GFP protein (FIG. 23). We have screened and sequenced specific strains and the circuit was functional by turning on these genes with cuminic acid and visualizing by exposing cells to blue light. We then performed fluorescent microscopy on a double transformant that have the whole gyp cluster as well as these constructs with GvpP and GvpQ tagged to Gfp.

Figures 24A, 24B, 24C, 24D:
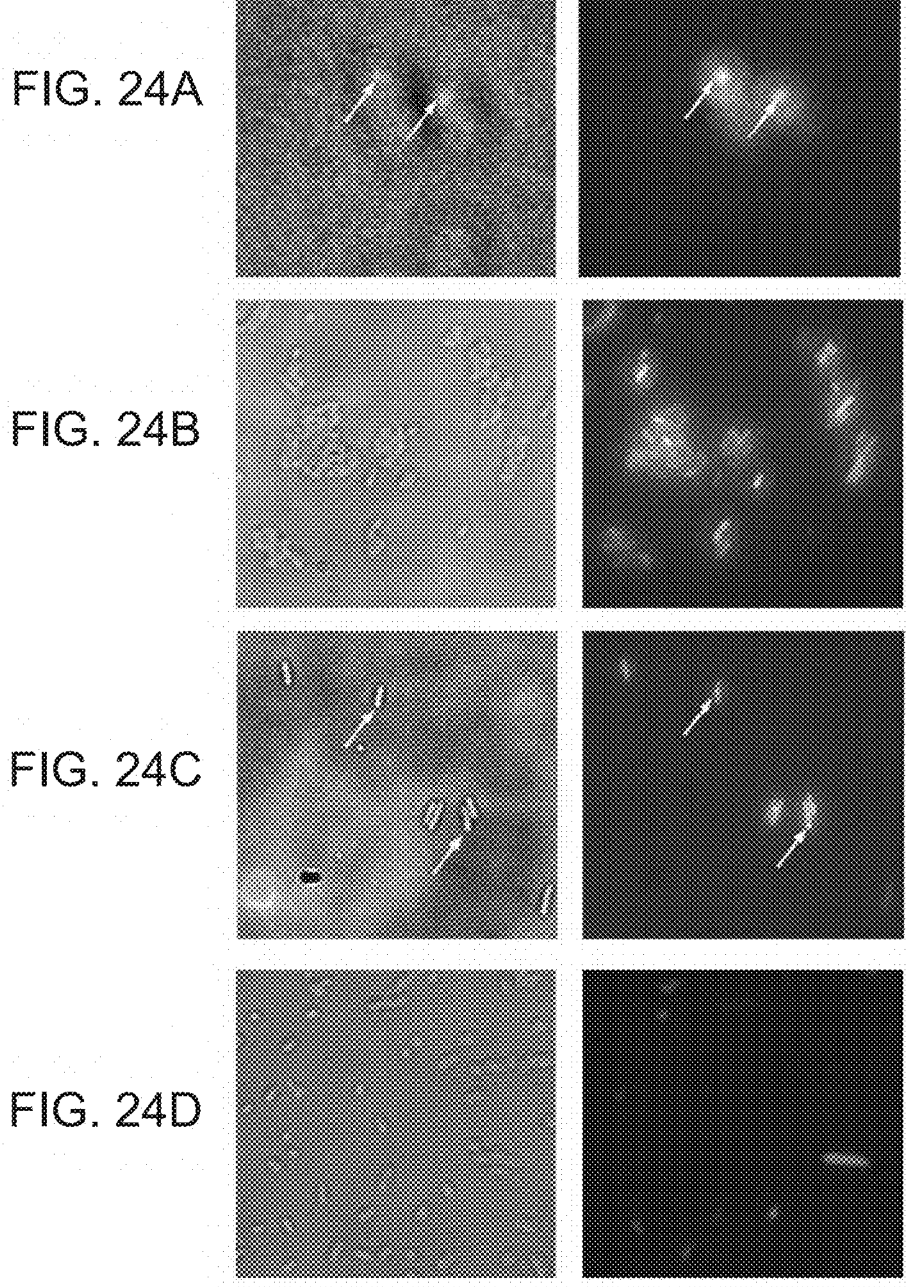
FIGS. 24A-24D. Brightfield and fluorescence images of cells with plasmid 506 and 495-498.

These anchoring surface protein in the gene cluster can be used to attach the CBD as well as other gene of interest. We tested the double transformants, that is, cells with both the gyp cluster (506 cells, FIG. 18*e*) and the genes gvpP fused to the gfp gene (plasmid 495-498) (FIG. 23). We used a fluorescence microscope with phase contrast images capability. For this set of images, we were looking for a correlation between fluoresce loci and the refractile bodies within the cells. In FIG. 24, we show tagging of the gas vesicles via the GvpP protein. For strain 495 and 497 in which GFP is at the N-terminus of the GvpP protein, the gfp is localizing within the GVs as indicated by the correlation between bright phase contrast images and the fluorescent loci. For strains, 496 and 498 which have the GFP protein at the C-terminus of GvpP protein, the Gfp is diffuse throughout the cells indicating the protein might not be folding properly, therefore, not localizing on the GVs. Within the gyp gene cluster of *B. megaterium*, we have identified the equivalent of gvpC in other gas vesicle producing cells which has never been reported before. The GvpQ tagged protein cells were grown overnight after induction because they were growing slower. We did not observe a GFP loci with these particular cells indicating these proteins are not localizing to the GVs, therefore, they might not be a structural protein or a proper candidate for attaching other proteins to the GVs.

Examples of the materials, strains, systems, methods and apparatuses discussed herein are not limited in application to the details of construction and the arrangement of components set forth in the following description or illustrated in the accompanying drawings. The systems, methods and apparatuses are capable of implementation in other examples and of being practiced or of being carried out in various ways. Examples of specific implementations are provided herein for illustrative purposes only and are not intended to be limiting. In particular, functions, components, elements, and features discussed in connection with any one or more examples are not intended to be excluded from a similar role in any other examples.

Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

Also, the phraseology and terminology used herein is for the purpose of description and should not be regarded as limiting. Any references to examples, components, elements, acts, or functions of the computer program products, systems and methods herein referred to in the singular may also embrace embodiments including a plurality, and any references in plural to any example, component, element, act, or function herein may also embrace examples including only a singularity. Accordingly, references in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. An aerogel material comprising:

a bacterial cellulose-based scaffold comprising a series of at least partially spaced fibers; and bacterially-derived gas vesicles located at least between fibers, wherein the gas vesicles comprise external cellulose binding modules (CBM) that anchor the gas vesicles to the fibers, and wherein the cellulose binding modules comprise CBM48 from at least one of *Komagataeibacter sucrofermentans* and *Micromonas pusilla*.

2. The material of claim 1, wherein the gas vesicles further comprise a polypeptide linker that promotes intermolecular reaction between the gas vesicles and the fibers.

3. The material of claim 1, wherein at least one of the scaffold and the gas vesicles further comprise external hydrophobicity modules that comprise a hydrophobic protein.

4. The material of claim 1, wherein at least one of the scaffold and the gas vesicles further comprise external fire resistance modules that comprise bacterially-produced melanin.

5. The material of claim 1, wherein the gas vesicles are produced from genetically engineered cells that comprise a gene cluster that encodes production of gas vesicles.

6. The material of claim 1, wherein the bacterial cellulose is produced by at least one of genetically modified bacteria and wild bacteria.

7. The material of claim 6, wherein the bacteria are grown in a liquid medium comprising water, sugar, tea, and vinegar.

8. The material of claim 7, wherein the bacteria grow on a surface of the liquid medium and oxygen levels below the surface are reduced from ambient.

9. The material of claim 7, wherein the pH of the medium is adjusted to a pH of between about 4.5 and about 5.5.

10. The material of claim 7, wherein the vinegar comprises apple cider vinegar.

11. The material of claim 1, made by spraying gas vesicles on the cellulose mat as it grows.

12. The material of claim 1, wherein gas vesicles are embedded in other polymers or fibrous matrix.

13. The material of claim 1, wherein the scaffold is in the form of sheets or pellets that are processed by ethanol exchange and then drying at room temperature, critical point drying, or by lyophilizing.

14. The material of claim 1, wherein the gas vesicles are from organisms that are different than the bacteria that make the cellulose.

15. The material of claim 1, made by soaking the cellulose in a bath that includes gas vesicles.

* * * * *